United States Patent
Hicks et al.

(10) Patent No.: US 11,014,920 B2
(45) Date of Patent: May 25, 2021

(54) FACTOR XIIA INHIBITORS

(71) Applicant: Merck Sharp & Dohme Corp., Rahway, NJ (US)

(72) Inventors: Jacqueline D. Hicks, Watchung, NJ (US); Brian Alexander McKittrick, New Vernon, NJ (US); Brent R. Whitehead, Morristown, NJ (US); Matthew Lombardo, Flemington, NJ (US); Xiaoqing Han, Edison, NJ (US); Jerry A. Taylor, Trenton, NJ (US); Hong Dong Chu, Livingston, NJ (US); Sung-Sau So, Verona, NJ (US); Peter Orth, Pittstown, NJ (US); Zhicai Wu, Montvale, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 10 days.

(21) Appl. No.: 16/461,825

(22) PCT Filed: Nov. 13, 2017

(86) PCT No.: PCT/US2017/061281
§ 371 (c)(1),
(2) Date: May 17, 2019

(87) PCT Pub. No.: WO2018/093716
PCT Pub. Date: May 24, 2018

(65) Prior Publication Data
US 2020/0262831 A1    Aug. 20, 2020

Related U.S. Application Data

(60) Provisional application No. 62/423,817, filed on Nov. 18, 2016.

(51) Int. Cl.
| | | |
|---|---|---|
| *C07D 417/14* | (2006.01) | |
| *A61P 7/02* | (2006.01) | |
| *C07D 401/12* | (2006.01) | |
| *C07D 409/12* | (2006.01) | |
| *C07D 409/14* | (2006.01) | |
| *C07D 417/12* | (2006.01) | |

(52) U.S. Cl.
CPC .............. *C07D 417/14* (2013.01); *A61P 7/02* (2018.01); *C07D 401/12* (2013.01); *C07D 409/12* (2013.01); *C07D 409/14* (2013.01); *C07D 417/12* (2013.01)

(58) Field of Classification Search
CPC combination set(s) only.
See application file for complete search history.

(56) References Cited

U.S. PATENT DOCUMENTS

| | | |
|---|---|---|
| 2005/0096328 A1 | 5/2005 | Wiley et al. |
| 2011/0065682 A1 | 3/2011 | Clasby et al. |
| 2014/0073573 A1 | 3/2014 | Herold et al. |
| 2016/0145263 A1 | 5/2016 | Pinto et al. |
| 2016/0257668 A1 | 9/2016 | Shao et al. |

FOREIGN PATENT DOCUMENTS

| | | |
|---|---|---|
| WO | 2000071516 A2 | 11/2000 |
| WO | 2012083436 A1 | 6/2012 |
| WO | WO2015047973 A1 | 4/2015 |
| WO | 2018093695 A1 | 5/2018 |

OTHER PUBLICATIONS

International Search Report and Written Opinion for PCT/US2017/061281, dated Jan. 16, 2018, 7 pages.
Supplementary European Search Report for 17871741.9, dated Apr. 14, 2020, 7 pages.

*Primary Examiner* — Valerie Rodriguez-Garcia
(74) *Attorney, Agent, or Firm* — Nicole M. Beeler; John C. Todaro

(57) ABSTRACT

The present invention provides a compound of Formula I and pharmaceutical compositions comprising one or more said compounds, and methods for using said compounds for treating or preventing thromboses, embolisms, hypercoagulability or fibrotic changes. The compounds are selective Factor XIIa inhibitors.

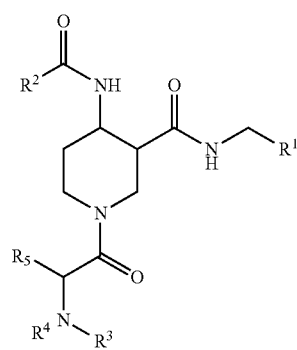

14 Claims, No Drawings

FACTOR XIIA INHIBITORS

CROSS REFERENCE TO RELATED APPLICATIONS

This application is a U.S. National Phase application under 35 U.S.C. § 371 of PCT Application No. PCT/US2017/061281 filed Nov. 13, 2017, which claims priority from U.S. Ser. No. 62/423,817 filed Nov. 18, 2016.

BACKGROUND OF THE INVENTION

Factor XIIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel, blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact ActivationPathway", Hemostasis and Thrombosis, pp. 103-122. Lippincott Williams & Wilkins (2001); Schmaier, A. H., "Contact Activation". Thrombosis and Hemorrhage, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)).

Patients undergoing coronary pulmonary bypass (CPB), excorporeal membrane oxygenation (ECMO) or hemodialysis are at risk for thrombotic events and complications due to increased inflammatory responses. FXIIa plays a unique dual role in initiating both the intrinsic coagulation pathway leading to thrombin mediated clot formation and also activating the Kallirein-Kinin pathway leading to increased levels of the inflammatory mediator, bradykinin, see Kenne. E.; Renne. T Factor XII: a drug target for safe interference with thrombosis and inflammation. *Drug Discovery Today* 2014, 19, 1459-146. Inhibitors of FXIIa seem ideally suited for the prevention of this device mediated thrombosis while lowering the incidence of complications during these procedures[7-9]. See, Renne, T., et al. In vivo roles of factor XII. *Blood* 2012, 120, 4296-4303; Kleinschnitz. C. et al., Targeting coagulation factor XII provides protection from pathological thrombosis in cerebral ischemia without interfering with hemostasis. *Journal of Experimental Medicine* 2006, 203, 513-518.

There is emerging evidence to show that in preclinical settings the inactivation of FXIIa by mAbs (see, Gruber. A., et al., Therapeutic antibodies against factor XII. In *Vanderbilt University USA: Aronora. Inc.; Oregon Health & Science University.* 2014; pp 91), infestin 4 (see, Worm, M., et al., The factor XIIa blocking antibody 3F7: a safe anticoagulant with anti-inflammatory activities. *Annals of Translational Medicine* 2015, 3, 247/241-247/245), the knockout or knockdown of FXII (see, Cheng, Q.; Tucker, E. I.; Pine, M. S.; Sisler, I.; Matafonov, A.; Sun, M.-f.; White-Adams, T. C.; Smith. S. A.; Hanson, S. R.; McCarty, O. J. T; Renne, T.; Gruber, A.; Gailani, D. A role for factor XIIa-mediated factor XI activation in thrombus formation in vivo. *Blood* 2010, 116, 3981-3989), leads to a selective prolongation of aPTT over PT, and reduced thrombosis formation. In some cases this has been shown to occur without increased bleeding. This feature distinguishes FXIIa from FIIa, FXa and FXIa and suggests that FXIIa inhibitors will have an improved safety profile with regard to bleeding (see, Gailani, D., et al., Factor XI and contact activation as targets for antithrombotic therapy. *Journal of Thrombosis and Haemostasis* 2015, 13, 1383-1395).

SUMMARY OF THE INVENTION

The present invention relates to compounds of Formula I:

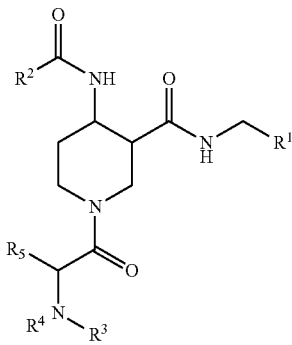

I and pharmaceutically acceptable salts thereof. The compounds of Formula I are selective Factor XIIa inhibitors, and as such may be useful in the treatment, inhibition or amelioration of one or more disease states that could benefit from inhibition of Factor XIIa, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The present invention relates to compounds of Formula I:

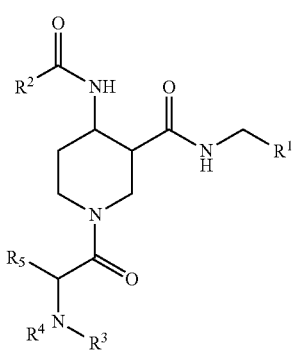

I wherein $R^1$ is aryl or heteroaryl, wherein said aryl and heteroaryl groups are optionally substituted with one to three substituents independently selected from the group consisting of hydroxyl, cyano, halo, $C_{1-3}$ alkyl, $O(C_{1-3}$ alkyl), $NH_2$, $CH_2NH_2$,$(C=O)NH_2$ or heteroaryl;

$R^2$ is aryl, heteroaryl,

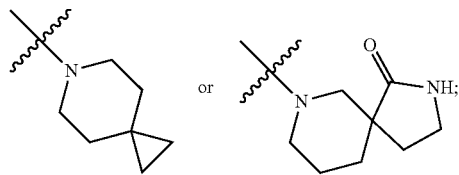 [SMILES: *N1CCC2(CC1)CC2 ; *N1CCCC2(CCNC2=O)C1]

wherein said aryl and heteroaryl groups are optionally substituted with one to three substituents independently selected from the group consisting of hydroxyl, oxo, cyano, halo, $C_{1-3}$ alkyl, $C_{1-3}$ haloalkyl, $O(C_{1-3}$ alkyl) and $NH_2$;
$R^3$ is hydrogen, $C_{1-3}$ alkyl,

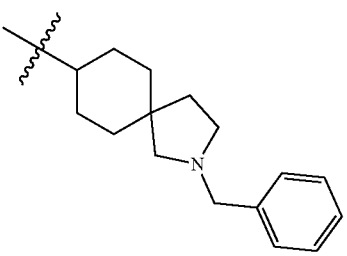 [SMILES: *C1CCC2(CC1)CCN(Cc1ccccc1)C2]

or $C_{3-7}$ cycloalkyl;
$R^4$ is hydrogen or $C_{1-4}$ alkyl;
$R^5$ is
(a) hydrogen,
(b) $CH_2$—$C_{3-6}$ cycloalkyl;
(c) piperidinyl, which is optionally substituted with hydroxyl, oxo, cyano, halo, $C_{1-3}$ alkyl, or
(d) $C_{1-4}$ alkyl which is optionally substituted with $NR^6R^7$, $N^+(CH_3)_3$, $NH(C=O)R^6$, $O(C=O)R^6$, $NR^6SO_2R^7$, $NHSO_2$cyclopropyl or heterocyclyl, wherein said heterocyclyl is optionally substituted with $R^6$;
$R^6$ is hydrogen or $C_{1-4}$ alkyl, which is optionally substituted with one to three substituents independently selected from the group consisting of halo and hydroxyl;
$R^7$ is hydrogen or $C_{1-3}$ alkyl, which is optionally substituted with one to three substituents independently selected from the group consisting of halo and hydroxyl;
or a pharmaceutically acceptable salt thereof.
In an embodiment of the invention, $R^1$ is indolyl, phenyl, thiazolyl or piperidinyl, wherein said groups are optionally substituted with one to three substituents independently selected from the group consisting of halo. $C_{1-3}$ alkyl, $NH_2$, or $CH_2NH_2$,$(C=O)NH_2$. In a class of the embodiment, $R^1$ is thiazolyl, which is optionally substituted with $C_{1-3}$ alkyl.
In an embodiment of the invention, $R^2$ isothiazolyl, phenyl, dihydroquinolinyl,

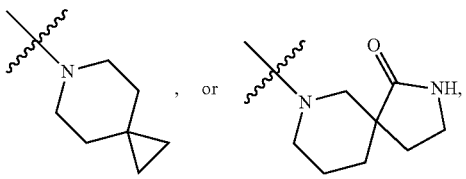 [SMILES: *N1CCC2(CC1)CC2 ; *N1CCCC2(CCNC2=O)C1]

or wherein said thiazolyl and phenyl, groups are optionally substituted with one to three substituents independently selected from the group consisting of halo and $C_{1-3}$ alkyl.

In an embodiment of the invention, R³ is cyclohexyl or

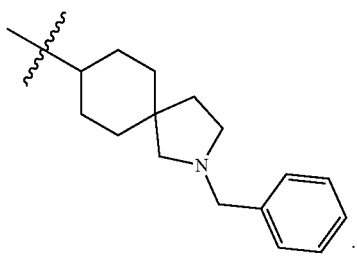 [SMILES: *C1CCC2(CC1)CCN(Cc1ccccc1)C2]

In an embodiment of the invention. R⁴ is hydrogen or methyl.

In an embodiment of the invention, R⁵ is $C_{1-4}$ alkyl which is optionally substituted with NR⁶R⁷, NH(C=O)R⁶, NHSO₂R⁷, NHSO₂cyclopropyl or heterocyclyl, wherein said heterocyclyl is optionally substituted with R⁷).

Reference to the preferred classes and subclasses set forth above is meant to include all combinations of particular and preferred groups unless stated otherwise.

Specific embodiments of the present invention include, but are not limited to the compounds identified herein as Examples 1 to 36, or pharmaceutically acceptable salts thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, treating inflammatory disorders, treating diabetic retinopathy and treating hereditary angioedema in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIIa inhibitors and may have therapeutic value in, for example, preventing coronary artery disease. The compounds are selective Factor XIIa inhibitors.

It will be understood that, as used herein, the present invention includes compounds of structural Formula I and the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides, dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I simultaneously contain acidic and basic groups in the molecule the invention also includes, in addition to the salt forms mentioned, inner salts or betaines (zwitterions).

The present invention encompasses all stereoisomeric forms of the compounds of Formula I. Unless a specific stereochemistry is indicated, the present invention is meant to comprehend all such isomeric forms of these compounds. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. When a particular configuration is depicted, that entantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

Unless a specific enationmer or diastereomer is indicated, the invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the transform as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^6$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the terms "alkyl" and "alkylene" are intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

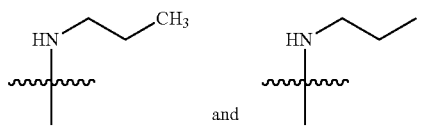

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on.

Except where noted, the term "halogen" or "halo" means fluorine, chlorine, bromine or iodine.

Except where noted, the term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, tetrahydroquinoline and 3-oxo-3,4dihydro-2N-benzo[b][1,4]thiazine. If the heteroaryl contains nitrogen atoms, it is understood that the corresponding N-oxides thereof are also encompassed by this definition.

Except where noted, the term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl.

"Celite®" (Fluka) diatomite is diatomaceous earth, and can be referred to as "celite".

Except where noted herein, structures containing substituent variables such as variable "R" below:

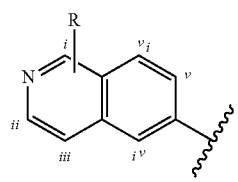

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also relates to medicaments containing at least one compound of the Formula I and/or of a pharmaceutically acceptable salt of the compound of the Formula I and/or an optionally stereoisomeric form of the compound of the Formula I or a pharmaceutically acceptable salt of the stereoisomeric form of the compound of Formula I, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor XIIa inhibition may be useful not only in the anticoagulant therapy of individuals having thrombotic conditions, but may be useful whenever inhibition of blood coagulation is required such as to prevent coagulation of stored whole blood and to prevent coagulation in other biological samples for testing or storage. Thus, the Factor XIIa inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula I and other surfaces which come into contact with blood in the body is possible.

The invention also relates to a process for the production of a medicament, which comprises bringing at least one compound of the Formula I into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIIa inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIIa inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XIIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIIa inhibitors can also be co-administered with suitable anticoagulants, including, but not limited to, other Factor XIIa inhibitors, thrombin inhibitors, thrombin receptor antagonists, factor VIIa inhibitors, factor Xa inhibitors, factor IXa inhibitors, factor XIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril): angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®, etc.); potassium sparing diuretics such as amiloride HCl, spironolactone, eplernanone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methyl-propyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine): potassium channel activators (e.g., nicorandil, pinacidil, cromakalim, minoxidil, aprilkalim, loprazolam): sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazosin, prazosin or alpha methyldopa): central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate: inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin, remogliflozin and sotagliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s): such pharmaceutical drugs could be used in a separate dosage form for concurrent or sequential administration with a compound of the invention, or the active agent(s) therein could be used in a fixed dose drug combination including a compound of the invention.

Typical doses of Factor XIIa inhibitors of the invention in combination with other suitable anti-platelet agents, anticoagulation agents, or thrombolytic agents may be the same as those doses of Factor XIIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e., prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

For purposes of this specification, the following abbreviations have the indicated meanings:
Ac acetyl
ACN acetonitrile
AcOH or HOAc acetic acid
aq aqueous
Bn benzyl
Boc or BOC tert-butoxycarbonyl
Bu butyl
Bz benzoyl
cBu cyclobutyl
Cbz benzyloxycarbonyl
cPr cyclopropyl
DCM dichloromethane
DIPEA or Hünig's base N,N-diisopropylethylamine
DMF dimethylformamide
DMSO dimethyl sulfoxide
Et ethyl
EtOAc ethyl acetate
FMOC fluorenylmethyloxycarbonyl
g grams
h hour
HATU   N,N,N',N'-tetramethyl-O-(7-azabenzotriazol-1-yl) uronium hexafluorophosphate
HOBt hydroxybenzotriazole
HPLC high-performance liquid chromatography
iPr isopropyl
KOTMS Potassium trimethylsilanolate
LAH lithium aluminium hydride
LCMS liquid chromatography mass spectrometry
Me methyl
MeOH methanol
mg milligrams
min minute
µL microliters mL milliliters
mmol millimoles
MS mass spectrometry
Ms methanesulfonyl (mesyl)
NMR nuclear magnetic resonance spectroscopy
Ph phenyl
Pr propyl
rac racemic mixture
RT or rt room temperature (ambient, about 25° C.)
SFC supercritical fluid chromatography
TBAF tetra-n-butylammonium fluoride
tBu tert-butyl
TEA triethylamine ($Et_3N$)
TFA trifluoroacetic acid
THF THF
TLC thin layer chromatography
TMS trimethylsilyl Also, UV is ultraviolet; W is watts; wt. % is percentage by weight; x g is times gravity; $\alpha_D$ is the specific rotation of polarized light at 589 nm; ° C. is degrees Celsius; % w/v is percentage in weight of the former agent relative to the volume of the latter agent; Hz is hertz; cpm is counts per minute; $\delta_H$ is chemical shift; d is doublet; dd is doublet of doublets; MHz is megahertz; MS is mass spectrum, and a mass spectrum obtained by ES-MS may be denoted herein by "LC-MS"; m/z is mass to charge ratio; n is normal. N is normal; nm is nanometer; nM is nanomolar.

"FXIIa IC50(nm)" is Human Factor XIIa IC50 (nm).

LCMS conditions: Waters Acquity UPLC/SQD MS system, Electrospray positive ionization mode: Column: Waters BEH C18 column, 1.0×50 mm, 1.7 um: MP: A:B/($H_2O$/0.05% TFA: ACN/0.05% TFA): Gradient: 0-2 min, (10-99)% B: Flow: 0.3 min/mL.

General Methods

Compounds of the present invention may be prepared using conventional techniques or according to the methodology outlined in the following general synthetic schemes.

General Scheme

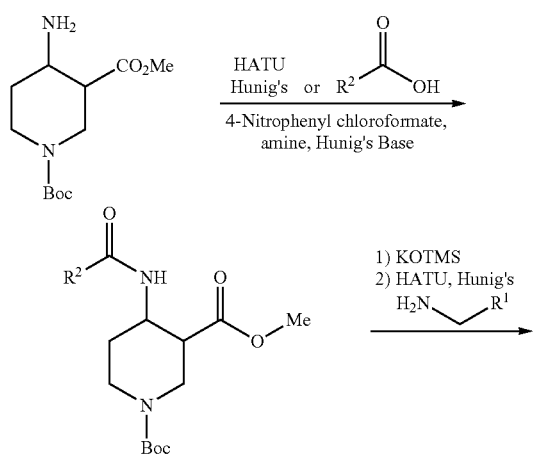

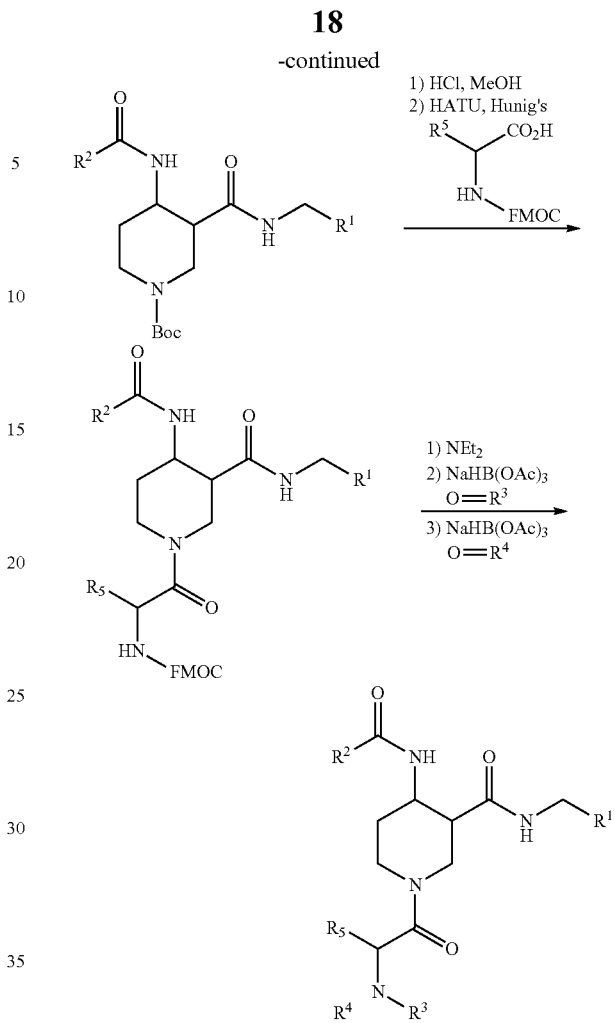

The compounds described can be prepared by functionalization of 1-(tert-butyl) 3-methyl 4-aminopiperidine-1,3-dicarboxylate at C4 using standard amide bond forming techniques, e.g. HATU. Alternatively, a urea can be installed at C4 using 4-Nitrophenyl chloroformate and desired amine. Hydrolysis of the ester at C3 followed by amide bond formation with the desired amine installs $R^1$. Boc-deprotection and amide bond formation with FMOC protected alpha-amino acid provides the functionalized core. FMOC-deprotection followed by reductive amination installs $R^3$ and $R^4$.

Intermediates

Intermediate 11

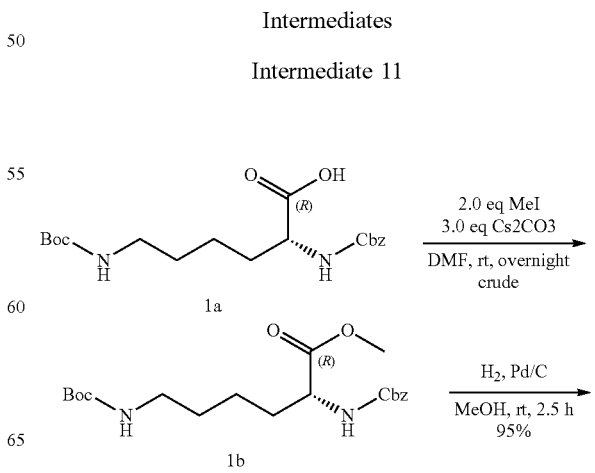

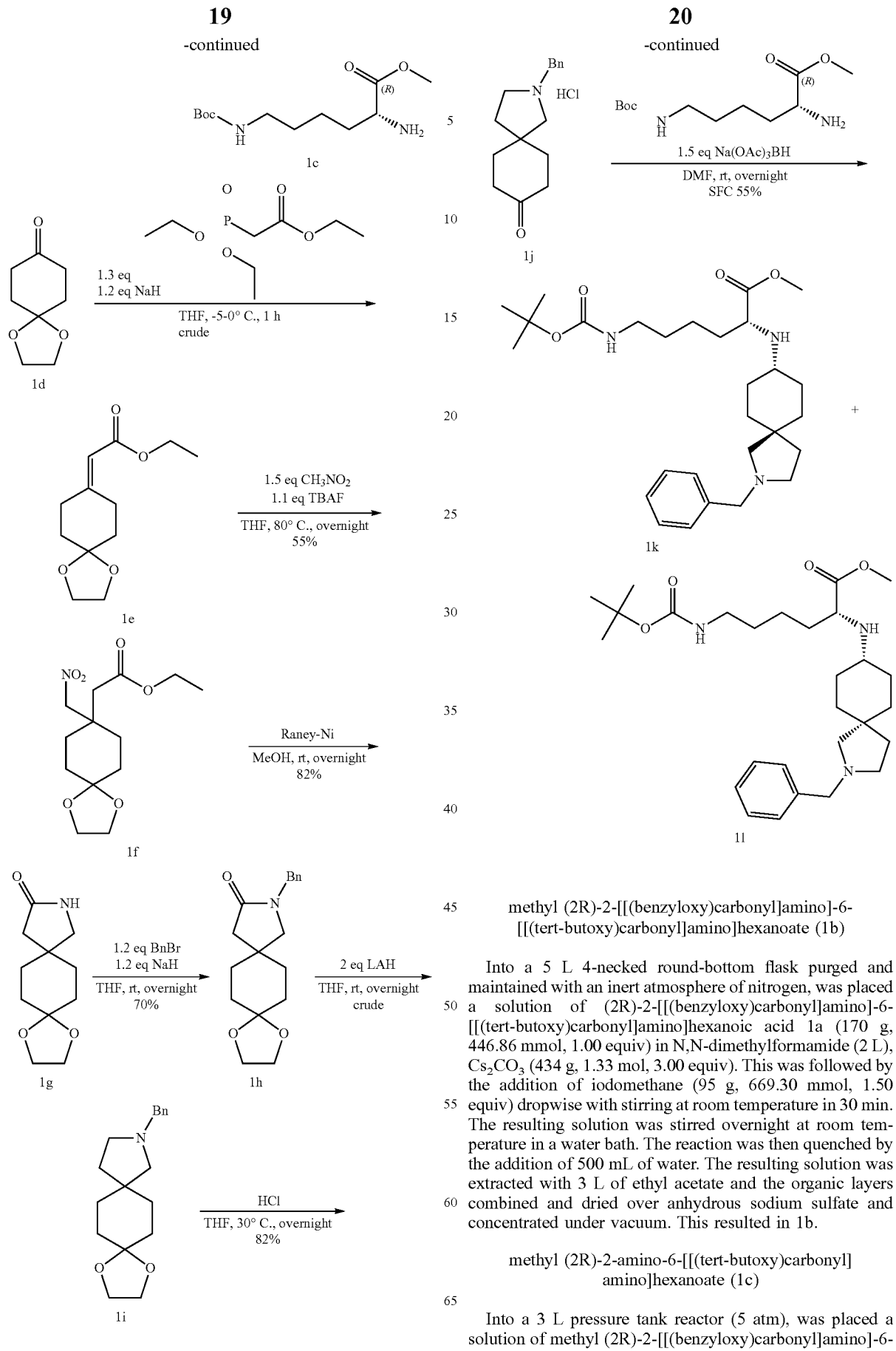

methyl (2R)-2-[[(benzyloxy)carbonyl]amino]-6-[[(tert-butoxy)carbonyl]amino]hexanoate (1b)

Into a 5 L 4-necked round-bottom flask purged and maintained with an inert atmosphere of nitrogen, was placed a solution of (2R)-2-[[(benzyloxy)carbonyl]amino]-6-[[(tert-butoxy)carbonyl]amino]hexanoic acid 1a (170 g, 446.86 mmol, 1.00 equiv) in N,N-dimethylformamide (2 L), Cs₂CO₃ (434 g, 1.33 mol, 3.00 equiv). This was followed by the addition of iodomethane (95 g, 669.30 mmol, 1.50 equiv) dropwise with stirring at room temperature in 30 min. The resulting solution was stirred overnight at room temperature in a water bath. The reaction was then quenched by the addition of 500 mL of water. The resulting solution was extracted with 3 L of ethyl acetate and the organic layers combined and dried over anhydrous sodium sulfate and concentrated under vacuum. This resulted in 1b.

methyl (2R)-2-amino-6-[[(tert-butoxy)carbonyl]amino]hexanoate (1c)

Into a 3 L pressure tank reactor (5 atm), was placed a solution of methyl (2R)-2-[[(benzyloxy)carbonyl]amino]-6-

[[(tert-butoxy)carbonyl]amino]hexanoate 1b (165 g, 418.29 mmol, 1.00 equiv) in methanol (1.5 L), Palladium carbon (16.5 g). The resulting solution was stirred overnight at room temperature under an atmosphere of hydrogen (balloon). The solids were filtered out. The filtrate was concentrated under vacuum. This resulted in 1c.

ethyl 2-[1,4-dioxaspiro[4.5]decan-8-ylidene]acetate (1e)

Into a 10 L 4-necked round-bottom flask purged and maintained with an inert atmosphere of nitrogen, was placed a solution of 1,4-dioxaspiro[4.5]decan-8-one 1d (350 g, 2.24 mol, 1.00 equiv) in tetrahydrofuran (3.5 L). This was followed by the addition of sodium hydride (115 g, 2.88 mol, 1.28 equiv, 60%) dropwise with stirring at 0° C. in 30 min. To this was added ethyl 2-(diethoxyphosphoryl)acetate (517.6 g, 2.31 mol, 1.03 equiv) dropwise with stirring at room temperature in 1 hr. The resulting solution was stirred for 4 h at room temperature. The reaction was then quenched by the addition of 4 L of water. The resulting solution was extracted with 8 L of ethyl acetate and the organic layers combined and dried over anhydrous sodium sulfate and concentrated under vacuum. This resulted in 1e.

ethyl 2-[8-(nitromethyl)-1,4-dioxaspiro[4.5]decan-8-yl]acetate (1f)

Into a 10 L 4-necked round-bottom flask purged and maintained with an inert atmosphere of nitrogen, was placed a solution of ethyl 2-[1,4-dioxaspiro[4.5]decan-8-ylidene] acetate 1e (350 g, 1.55 mol, 1.00 equiv) in tetrahydrofuran (3.5 L) at room temperature. This was followed by the addition of TBAF (445 g, 1.70 mol, 1.10 equiv), nitromethane (142 g, 2.33 mol, 1.50 equiv). The resulting solution was stirred overnight at 80° C. in an oil bath. The reaction was then quenched by the addition of 4 L of water. The resulting solution was extracted with 8 L of ethyl acetate and the organic layers combined and dried over anhydrous sodium sulfate and concentrated under vacuum. The residue was applied onto a silica gel column with ethyl acetate/petroleum ether (1:20-1:8). This resulted in 1f.

1,4-dioxa-10-azadispiro[4.2.4^[8].2^[5]]tetradecan-11-one (1g)

Into a 20 L pressure tank reactor (5 atm), was placed a solution of ethyl 2-[8-(nitromethyl)-1,4-dioxaspiro[4.5]decan-8-yl]acetate 1f (230 g, 800.53 mmol, 1.00 equiv) in methanol (10 L), Raney-Ni (50 g). The resulting solution was stirred overnight at room temperature under an atmosphere of hydrogen (balloon). The solids were filtered out. The filtrate was concentrated under vacuum. This resulted in 1g.

10-benzyl-1,4-dioxa-10-azadispiro[4.2.4^[8].2^[5]] tetradecan-11-one (1h)

Into a 5 L 4-necked round-bottom flask purged and maintained with an inert atmosphere of nitrogen, was placed a solution of 1,4-dioxa-10-azadispiro[4.2.4^[8].2^[5]]tetradecan-11-one 1g (140 g, 662.70 mmol, 1.00 equiv) in tetrahydrofuran (2 L). This was followed by the addition of sodium hydride (20 g, 500 mmol, 0.75 equiv) in several batches at 0° C. in 20 min. To this was added (bromomethyl) benzene (135 g, 789.32 mmol, 1.20 equiv) dropwise with stirring at 0° C. in 30 min. The resulting solution was stirred overnight at room temperature in a water bath. The reaction was then quenched by the addition of 2 L of water. The resulting solution was extracted with 5 L of ethyl acetate and the organic layers combined and dried over anhydrous sodium sulfate and concentrated under vacuum. The residue was applied onto a silica gel column with ethyl acetate/ petroleum ether (1:1). This resulted in 1h.

10-benzyl-1,4-dioxa-10-azadispiro[4.2.4^[8].2^[5]] tetradecane (1i)

Into a 5 L 4-necked round-bottom flask purged and maintained with an inert atmosphere of nitrogen, was placed a solution of 10-benzyl-1,4-dioxa-10-azadispiro[4.2.4^[8]. 2^[5]]tetradecan-11-one 1h (140 g, 464.53 mmol, 1.00 equiv) in tetrahydrofuran (1.4 L). This was followed by the addition of LAH (35.3 g, 930.17 mmol, 2.00 equiv) in several batches at 0° C. in 20 min. The resulting solution was stirred overnight at room temperature in a water bath. The reaction mixture was cooled to 0° C. with an ice/salt bath. The reaction was then quenched by the addition of 40 mL of water. The pH value of the solution was adjusted to 7 with 40 Ml sodium hydroxide (15%). Then the mixture was stirred 1 hour at room temperature. The solids were filtered out. The filtrate was concentrated under vacuum. This resulted in 1i.

2-benzyl-2-azaspiro[4.5]decan-8-one hydrochloride (1j)

Into a 20-L pressure tank reactor, was placed a solution of 10-benzyl-1,4-dioxa-10-azadispiro[4.2.4^[8].2^[5]]tetradecane 1i (100 g, 347.95 mmol, 1.00 equiv) in tetrahydrofuran (1 L). This was followed by the addition of hydrogen chloride (4 L) dropwise with stirring at 0° C. in 2 hr. The resulting solution was stirred overnight at room temperature. The pH value of the solution was adjusted to 7 with sodium carbonate (30%). The resulting solution was extracted with 8 L of ethyl acetate and the organic layers combined and dried over anhydrous sodium sulfate and concentrated under vacuum. The residue was washed with 100 mL of MTBE. The solids were collected by filtration. This resulted in 1j.

methyl (2R)-6-[[(tert-butoxy)carbonyl]amino]-2-[[(5r,8r)-2-benzyl-2-azaspiro[4.5]decan-8-yl]amino] hexanoate (1k) and methyl (2R)-6-[[(tert-butoxy) carbonyl]amino]-2-[[(5s,8s)-2-benzyl-2-azaspiro [4.5]decan-8-yl]amino]hexanoate (1l)

Into a 5-L 4-necked round-bottom flask purged and maintained with an inert atmosphere of nitrogen, was placed a solution of 2-benzyl-2-azaspiro[4.5]decan-8-one hydrochloride 1j (80 g, 285.91 mmol, 1.00 equiv, 95%) in dichloromethane (1.5 L), methyl (2R)-2-amino-6-[[(tert-butoxy) carbonyl]amino]hexanoate 1c (86.2 g, 331.12 mmol, 1.16 equiv). This was followed by the addition of bis(acetyloxy) boranyl acetate sodium (121 g, 573.64 mmol, 2.00 equiv) in several batches at 0° C. in 30 min. The resulting solution was stirred overnight at room temperature in a water bath. The pH value of the solution was adjusted to 8 with sodium bicarbonate (40%). The resulting solution was extracted with 3 L of dichloromethane and the organic layers combined. The resulting mixture was washed with 1 L of sodium chloride. The mixture was dried over anhydrous sodium sulfate and concentrated under vacuum. The crude product (100 g) was purified by Prep-SFC with the following conditions: Column, CHIRALPAK AD-33*100 mm, 3umUPCAD3SCK-SC002; mobile phase, ethanol (0.1% DEA) 20; Detector, 220 nm. This resulted in 1k and 1l.

LC-MS-1k: (ES, m/z): 488 [M−H]⁻

H-NMR-1k: (400 MHz, Methanol-d4, ppm): δ 7.30 (m, 5H), 3.70 (d, J=3.5 Hz, 5H), 3.35 (m, 1H), 3.00 (t, J=6.8 Hz, 2H), 2.59 (t, J=6.9 Hz, 2H), 2.44 (s, 2H), 2.31 (tt, J=10.5, 3.7 Hz, 1H), 1.80 (m, 1H), 1.73-1.66 (m, 3H), 1.60 (dt, J=13.5, 7.1 Hz, 4H), 1.43 (s, 11H), 1.30 (tdd, J=12.5, 5.8, 2.9 Hz, 5H), 1.22-0.97 (m, 2H).

LC-MS-1l: (ES, m/z): 488 [M−H]⁻

H-NMR-1l: ((400 MHz, Methanol-d4, ppm): 57.33-7.25 (m, 5H), 4.87 (s, 5H), 3.70 (d, J=15.2 Hz, 5H), 3.01 (t, J=6.8 Hz, 2H), 2.65 (t, J=6.9 Hz, 2H), 2.50 (s, 2H), 2.33 (dtd, J=12.6, 8.9, 4.7 Hz, 1H), 1.78 (dd, J=12.0, 4.0 Hz, 1H), 1.64 (m, 7H), 1.42 (m, 11H), 1.28 (m, 6H).

Intermediate 2c

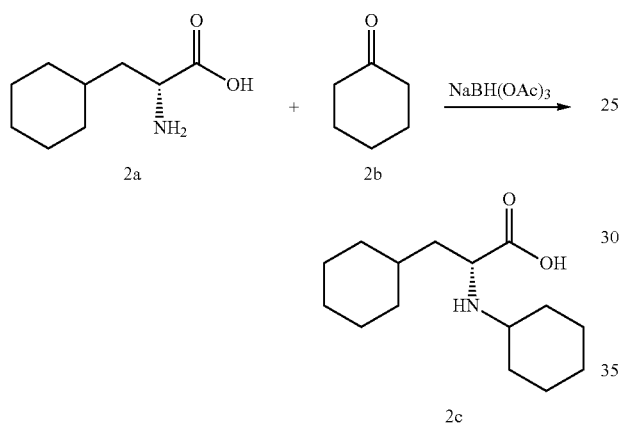

Sodium triacetoxyborohydride (2.475 g, 11.68 mmol) was added to a stirred mixture of (R)-2-amino-3-cyclohexylpropanoic acid 2a (1.00 g, 5.84 mmol), cyclohexanone 2b (0.908 mL, 8.76 mmol) and AcOH (0.435 mL, 7.59 mmol) in a mixture of THF (10 mL)/MeOH (0.5 mL) and the reaction was allowed to stir at room temperature for 1 h. After 1 h, water was added upon which some solids precipitated out and was filtered. The solid was triturated with water followed by CH₂Cl₂ and dried overnight to yield 2c. The product was used as such without further purification. LC-MS: calculated for $C_{15}H_{27}NO_2$ 253, observed m/e: 254 (M+H)⁺; (Rt 0.87/2.0 min).

Intermediate 3d

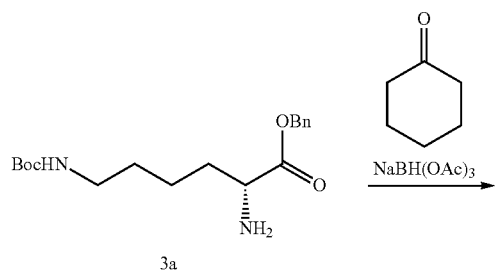

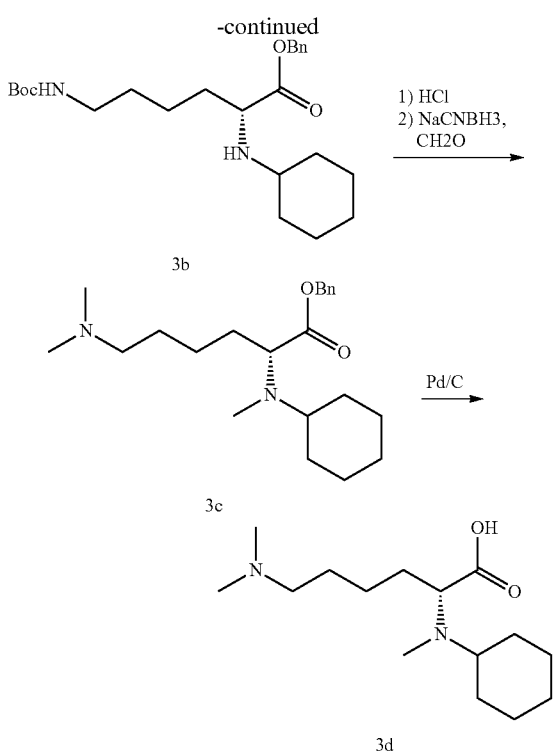

benzyl N6-(tert-butoxycarbonyl)-N2-cyclohexyl-D-lysinate (3b)

Cyclohexanone (0.978 g, 9.97 mmol) was added to benzyl N6-(tert-butoxycarbonyl)-D-lysinate (134 g, 3.99 mmol) in 25 mL of DCE. Sodium triacetoxyborohydride (2.53 g, 11.96 mmol) was then added to the solution at rt. The reaction mixture was stirred at room temperature for 2 hrs. The reaction was quenched with H₂O and extracted with DCM. The organic layer was dried with MgSO₄, filtered, and concentrated. The residue was purified by column chromatography on silica gel Teledyne Isco RediSep[12 g prepacked] eluting with 0% EtOAc/EtOH=3/1 to 40% in hexanes. Concentration of desired fractions provided 3b. LC-MS: calculated for 418, observed m/e: 420 (M+H)⁺; (Rt 1.04/2.0 min).

benzyl N2-cyclohexyl-N2,N6,N6-trimethyl-D-lysinate (3c)

To benzyl N6-(tert-butoxycarbonyl)-N2-cyclohexyl-D-lysinate (1.495 g, 3.57 mmol) in 15 mL of MeOH was added 9 mL of 4 M HCl in dioxane. The mixture was then stirred at room temperature for 2 hrs. The mixture was then concentrated and lyophilized. The crude was used for next step without further purification.

To benzyl cyclohexyl-D-lysinate in MeOH (30 mL) was added formaldehyde (37% in MeOH, 2.90 g, 2.66 mL). Then polymer bond cyanoborohydride (2 mmol/g, 3 g) was added. The mixture was then stirred for 1 hr. The mixture was filtered through a celite pad and concentrated. The residue was purified by column chromatography on silica gel Teledyne Isco RediSep[40 g prepacked] eluting with 0% EtOAc/ EtOH=3/1 to 100% in hexanes. Concentration of the desired fraction provided 3c. LC-MS: calculated for $C_{22}H_{36}N_2O_2$ 360, observed m/e: 361 (M+H)+; (Rt 0.31/2.0 min).

N2-cyclohexyl-N2,N6,N6-trimethyl-D-lysine (3d)

A solution of benzyl N2-cyclohexyl-N2,N6,N6-trimethyl-D-lysinate (2.20 g, 6.10 mmol) in 50 mL of MeOH was stirred under $H_2$ at room temperature for 1.5 hours. The mixture was filtered through celite and the filter cake was washed with MeOH. The filtrate was concentrated. LC-MS: calculated for $C_{15}H_{30}N_2O_2$ 270, observed m/e: 271 (M+H)+; (Rt 0.31/2.0 min).

Example 1

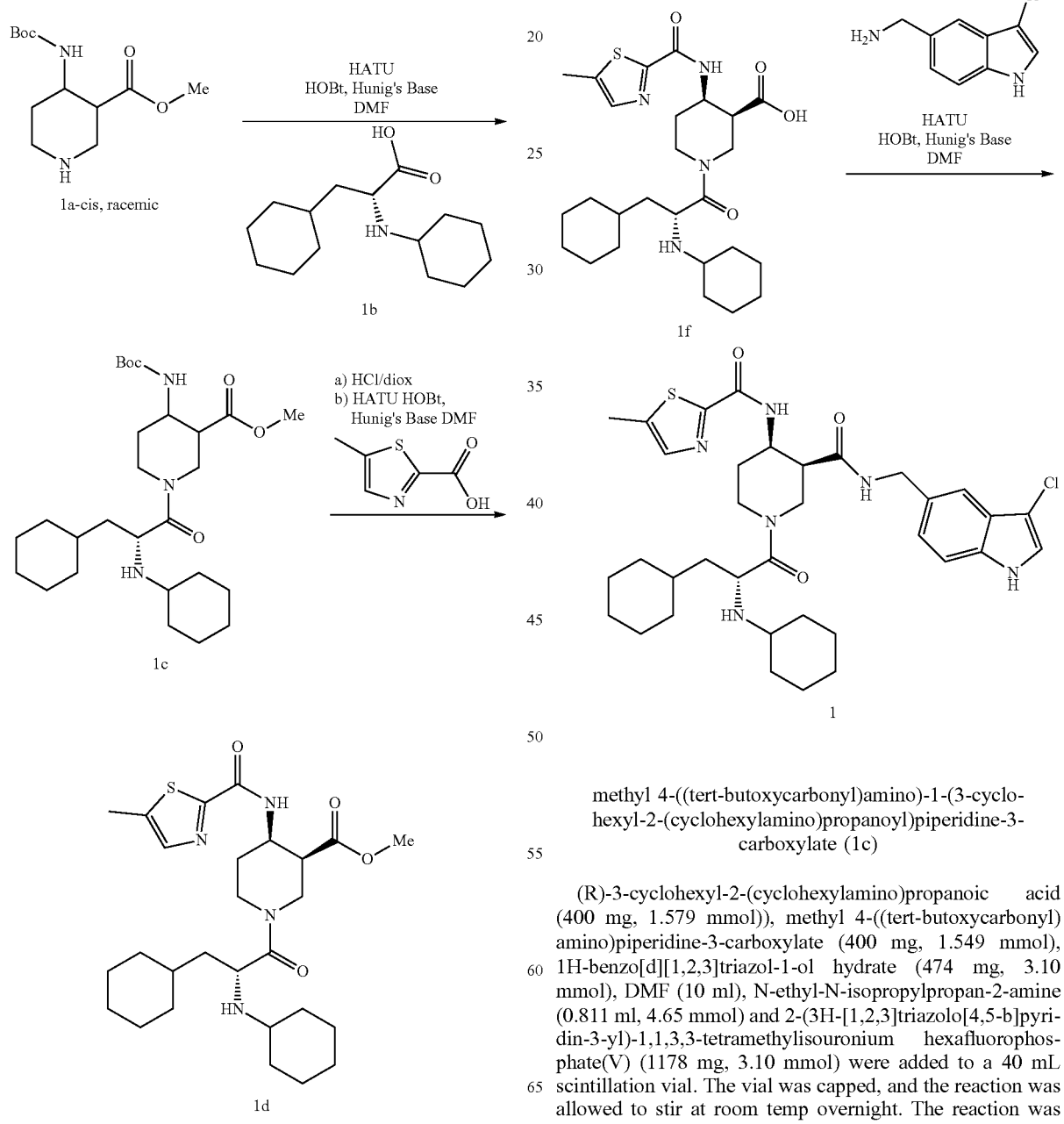

methyl 4-((tert-butoxycarbonyl)amino)-1-(3-cyclohexyl-2-(cyclohexylamino)propanoyl)piperidine-3-carboxylate (1c)

(R)-3-cyclohexyl-2-(cyclohexylamino)propanoic acid (400 mg, 1.579 mmol)), methyl 4-((tert-butoxycarbonyl)amino)piperidine-3-carboxylate (400 mg, 1.549 mmol), 1H-benzo[d][1,2,3]triazol-1-ol hydrate (474 mg, 3.10 mmol), DMF (10 ml), N-ethyl-N-isopropylpropan-2-amine (0.811 ml, 4.65 mmol) and 2-(3H-[1,2,3]triazolo[4,5-b]pyridin-3-yl)-1,1,3,3-tetramethylisouronium hexafluorophosphate(V) (1178 mg, 3.10 mmol) were added to a 40 mL scintillation vial. The vial was capped, and the reaction was allowed to stir at room temp overnight. The reaction was diluted with ethyl acetate, washed with water and brine (aqueous). The organic layer was extracted out and concentrated. The crude was purified via ISCO (split crude in half, ran two separate columns): (0-100% ethyl acetate/hexane for 20 minutes, then 0-20% methanol/dichloromethane for an additional 10 minutes, 30 minutes total, 80 g column) to provide 1c. LC-MS: calculated for $C_{19}H_{14}ClN_3O_2S$: 493, observed m/e: 494.6 (M+H)$^+$; (Rt 1.1/2.0 min).

methyl (3S,4R)-1-((R)-3-cyclohexyl-2-(cyclohexylamino)propanoyl)-4-(5-methylthiazole-2-carboxamido)piperidine-3-carboxylate (1d) and methyl (3R,4S)-1-((R)-3-cyclohexyl-2-(cyclohexylamino)propanoyl)-4-(5-methylthiazole-2-carboxamido)piperidine-3-carboxylate (1e)

To a round bottom flask was added the following: methyl 4-amino-1-((R)-3-cyclohexyl-2-(cyclohexylamino)propanoyl)piperidine-3-carboxylate dihydrochloride (5.3 g, 11.36 mmol)), 5-methylthiazole-2-carboxylic acid (1.627 g, 11.36 mmol), 1H-benzo[d][1,2,3]triazol-1-ol hydrate (3.48 g, 22.72 mmol)DMF (35 ml), N-ethyl-N-isopropylpropan-2-amine (9.92 ml, 56.8 mmol) and 2-(3H-[1,2,3]triazolo[4,5-b]pyridin-3-yl)-1,1,3,3-tetramethylisouronium hexafluorophosphate(V) (8.64 g, 22.72 mmol). The vial was capped, and the reaction was allowed to stir at room temp overnight. The reaction was diluted with ethyl acetate, washed with water and brine (aqueous). The organic layer was extracted out and concentrated. The crude was purified via ISCO (0-75% ethyl acetate/hexane for 10 minutes, 75-100% ethyl acetate/hexane for 10 minutes, 100% ethyl acetate for 10 minutes, 30 minutes total, 330 g column). Pure isomer 1 fractions were combined and concentrated to provide 1d (11%). Pure isomer 2 fractions were combined and concentrated to provide 1e (19%). LC-MS for 1d: calculated for $C_{27}H_{42}N_4O_4S$ 518, observed m/e: 519.8 (M+H)$^+$; (Rt 1.20/2.0 min). LC-MS for 1e: calculated for $C_{27}H_{42}N_4O_4S$ 518, observed m/e: 519.8 (M+H)$^+$; (Rt 1.22/2.0 min).

(3S,4R)-1-((R)-3-cyclohexyl-2-(cyclohexylamino) propanoyl)-4-(5-methylthiazole-2-carboxamido) piperidine-3-carboxylic acid (1f)

To a round bottom flask containing (3S,4R)-methyl 1-((R)-3-cyclohexyl-2-(cyclohexylamino)propanoyl)-4-(5-methylthiazole-2-carboxamido)piperidine-3-carboxylate (662 mg, 1.276 mmol) was added water (6 ml)), THF (4 mL) and potassium trimethylsilanolate (491 mg, 3.83 mmol). The reaction was allowed to stir at room temp for 3 hr. The reaction was quenched with 10 mL 1N HCl. Then, 30 mL water and 50 mL ethyl acetate were added. The ethyl acetate layer was extracted out (three times), dried under sodium sulfate, filtered and concentrated to provide 1f. LC-MS for 1f: calculated for $C_{27}H_{42}N_4O_4S$ 504, observed m/e: 505 (M+H)$^+$; (Rt 1.10/2.0 min).

N-((3S,4R)-3-(((3-chloro-1H-indol-5-yl)methyl) carbamoyl)-1-((R)-3-cyclohexyl-2-(cyclohexylamino)propanoyl)piperidin-4-yl)-5-methylthiazole-2-carboxamide (1)

To a 40 mL scintillation vial was added the following: (3S,4R)-1-((R)-3-cyclohexyl-2-(cyclohexylamino)propanoyl)-4-(5-methylthiazole-2-carboxamido)piperidine-3-carboxylic acid (3 mg, 5.94 μmol), (3-chloro-1H-indol-5-yl)methanamine hydrochloride (6.45 mg, 0.030 mmol), 1H-benzo[d][1,2,3]triazol-1-ol hydrate (1.821 mg, 0.012 mmol), DMF (1 ml)), N-ethyl-N-isopropylpropan-2-amine (2.305 mg, 0.018 mmol) and 2-(3H-[1,2,3]triazolo[4,5-b]pyridin-3-yl)-1,1,3,3-tetramethylisouronium hexafluorophosphate(V) (4.52 mg, 0.012 mmol). The vial was capped, and the reaction was allowed to stir at room temp for 30 mins. After LCMS, it was confirmed that the desired product was observed. The crude was diluted with water (0.5% TFA) and acidified with a few drops of TFA. The crude was purified via Gilson (17 minute run, can $H_2O$/0.05% TFA system): (0-12 minutes: 0-100% organic ramp), 12-14 minutes: 100% organic, 14-14.5 minutes: ramps down to 0% organic, 14.5-17 minutes: 0% organic). Fractions from 10.25-10.55 minutes were concentrated to provide 1. LC-MS for 1: calculated for $C_3H_{47}ClN_6O_3S$ 666, observed m/e: 667 (M+H)$^+$; (Rt 1.11/2.0 min).

By using the procedures similar to those described above, and appropriate starting materials, the following compounds were synthesized and characterized.

| Compound number | Structure | Name | Exact Mass [M + H]+ | FXIIa IC50 (nM) |
|---|---|---|---|---|
| 1 | 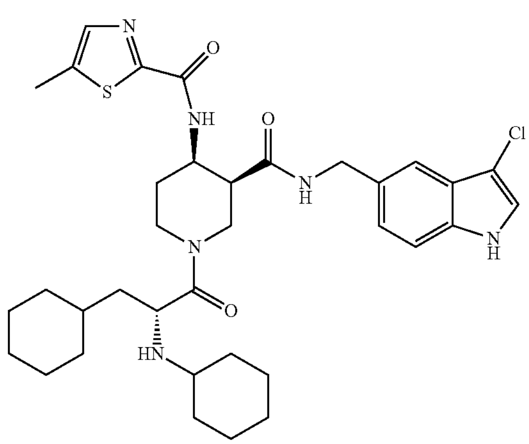 [SMILES: Cc1cnc(C(=O)N[C@@H]2CCN(C(=O)[C@@H](CC3CCCCC3)NC3CCCCC3)C[C@@H]2C(=O)NCc2ccc3[nH]cc(Cl)c3c2)s1] | (3S,4R)-N-[(3-chloro-1H-indol-5-yl)methyl]-1-(N,3-dicyclohexyl-D-alanyl)-4-{[(5-methyl-1,3-thiazol-2-yl)carbonyl]amino}piperidine-3-carboxamide | 667 | 49.2 |

-continued

| Compound number | Structure | Name | Exact Mass [M + H]+ | FXIIa IC50 (nM) |
|---|---|---|---|---|
| 2 | 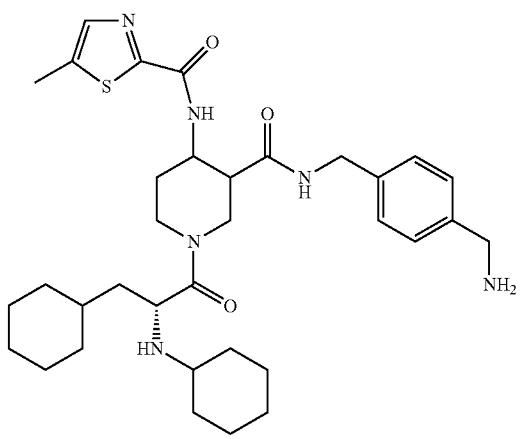 [SMILES: Cc1cnc(C(=O)NC2CCN(C(=O)[C@@H](CC3CCCCC3)NC3CCCCC3)CC2C(=O)NCc2ccc(CN)cc2)s1] | N-[4-(aminomethyl)benzyl]-1-(N,3-dicyclohexyl-D-alanyl)-4-{[(5-methyl-1,3-thiazol-2-yl)carbonyl]amino}piperidine-3-carboxamide | 623 | 73.3 |
| 3 | 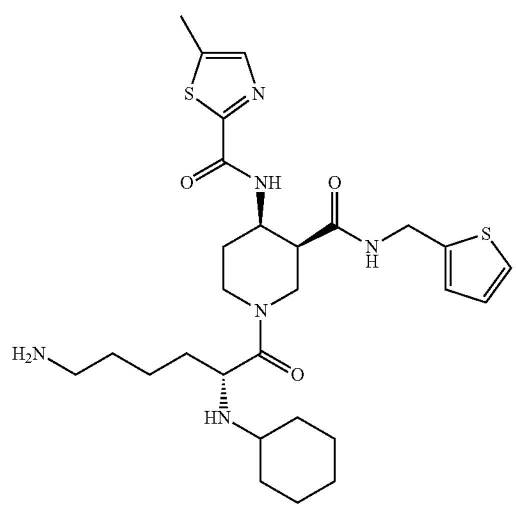 [SMILES: Cc1cnc(C(=O)N[C@@H]2CCN(C(=O)[C@@H](CCCCN)NC3CCCCC3)C[C@@H]2C(=O)NCc2cccs2)s1] | (3S,4R)-1-(N~2~-cyclohexyl-D-lysyl)-4-{[(5-methyl-1,3-thiazol-2-yl)carbonyl]amino}-N-(thiophen-2-ylmethyl)piperidine-3-carboxamide | 575 | 108.7 |
| 4 | 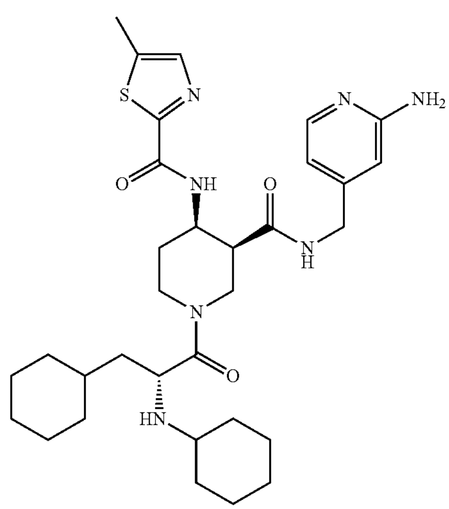 [SMILES: Cc1cnc(C(=O)N[C@@H]2CCN(C(=O)[C@@H](CC3CCCCC3)NC3CCCCC3)C[C@@H]2C(=O)NCc2ccnc(N)c2)s1] | (3S,4R)-N-[(2-aminopyridin-4-yl)methyl]-1-(N,3-dicyclohexyl-D-alanyl)-4-{[(5-methyl-1,3-thiazol-2-yl)carbonyl]amino}piperidine-3-carboxamide | 610 | 65.1 |

-continued

| Compound number | Structure | Name | Exact Mass [M + H]+ | FXIIa IC50 (nM) |
|---|---|---|---|---|
| 5 | 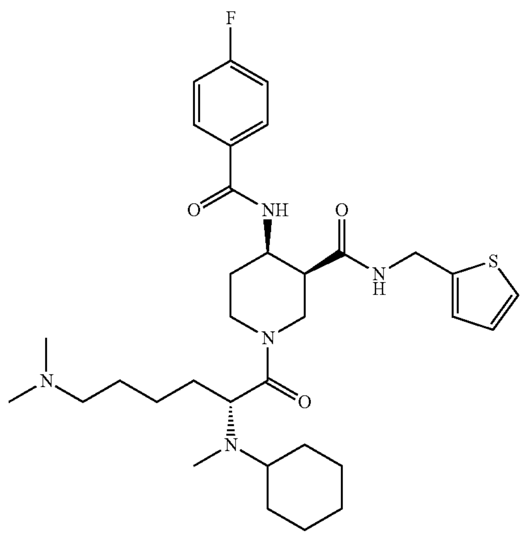 [SMILES: CN(C)CCCC[C@H](C(=O)N1CC[C@@H](NC(=O)c2ccc(F)cc2)[C@@H](C(=O)NCc2cccs2)C1)N(C)C1CCCCC1] | (3S,4R)-1-(N~2~-cyclohexyl-N~2~,N~6~,N~6~-trimethyl-D-lysyl)-4-{[(3,4-difluoro-phenyl)carbonyl]amino}-N-(thiophen-2-ylmethyl)piperidine-3-carboxamide | 632 | 71.6 |
| 6 | 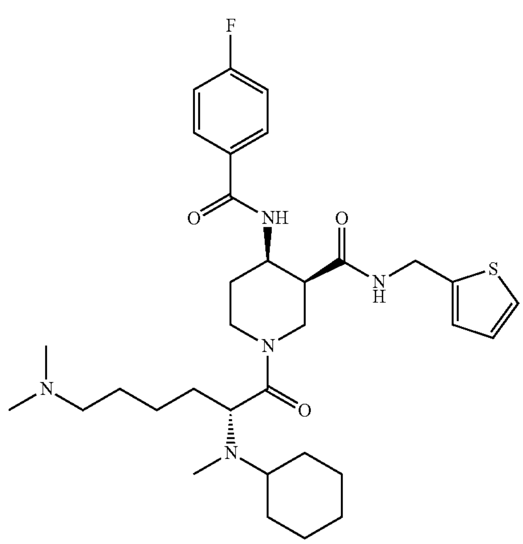 [SMILES: CN(C)CCCC[C@H](C(=O)N1CC[C@@H](NC(=O)c2ccc(F)cc2)[C@@H](C(=O)NCc2cccs2)C1)N(C)C1CCCCC1] | (3S,4R)-1-(N~2~-cyclohexyl-N~2~,N~6~,N~6~-trimethyl-D-lysyl)-4-{[(4-fluoro-phenyl)carbonyl]amino}-N-(thiophen-2-ylmethyl)piperidine-3-carboxamide | 614 | 98.3 |

-continued

| Compound number | Structure | Name | Exact Mass [M + H]+ | FXIIa IC50 (nM) |
|---|---|---|---|---|
| 7 | 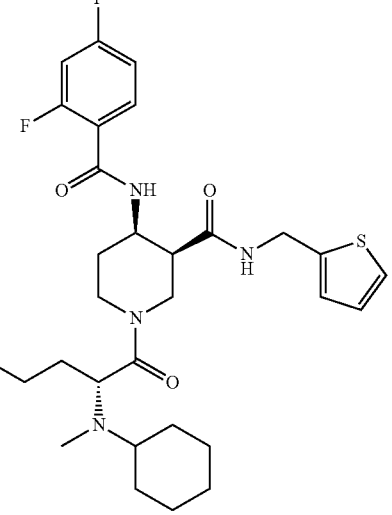 | (3S,4R)-1-(N~2~-cyclohexyl-N~2~,N~6~,N~6~-trimethyl-D-lysyl)-4-{[(2,4-difluorophenyl)carbonyl]amino}-N-(thiophen-2-ylmethyl)piperidine-3-carboxamide | 632 | 18.7 |
| 8 | 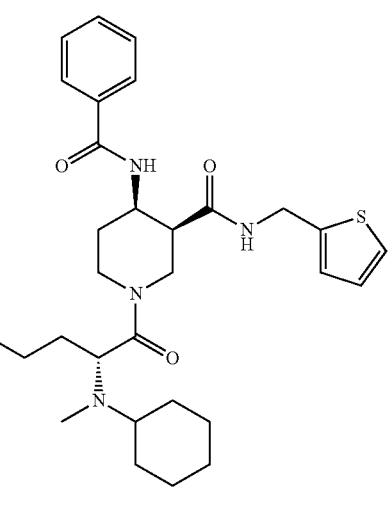 | (3S,4R)-1-(N~2~-cyclohexyl-N~2~,N~6~,N~6~-trimethyl-D-lysyl)-4-[(phenylcarbonyl)amino]-N-(thiophen-2-ylmethyl)piperidine-3-carboxamide | 596 | 60.2 |
| 9 | 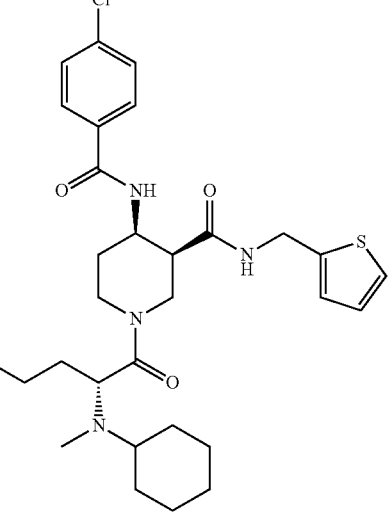 | (3S,4R)-4-{[(4-chlorophenyl)carbonyl]amino}-1-(N~2~-cyclohexyl-N~2~,N~6~,N~6~-trimethyl-D-lysyl)-N-(thiophen-2-ylmethyl)piperidine-3-carboxamide | 630 | 11.5 |

| Compound number | Structure | Name | Exact Mass [M + H]+ | FXIIa IC50 (nM) |
|---|---|---|---|---|
| 10 | 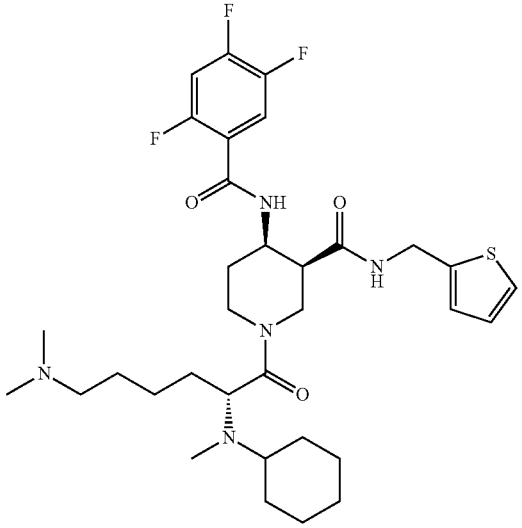 [SMILES: CN(C)CCCC[C@H](C(=O)N1CC[C@@H](NC(=O)c2cc(F)c(F)cc2F)[C@@H](C(=O)NCc2cccs2)C1)N(C)C1CCCCC1] | (3S,4R)-1-(N~2~-cyclohexyl-N~2~,N~6~,N~6~-trimethyl-D-lysyl)-N-(thiophen-2-ylmethyl)-4-{[(2,4,5-trifluoro-phenyl)carbonyl]amino}piperidine-3-carboxamide | 650 | 29.2 |
Example 11
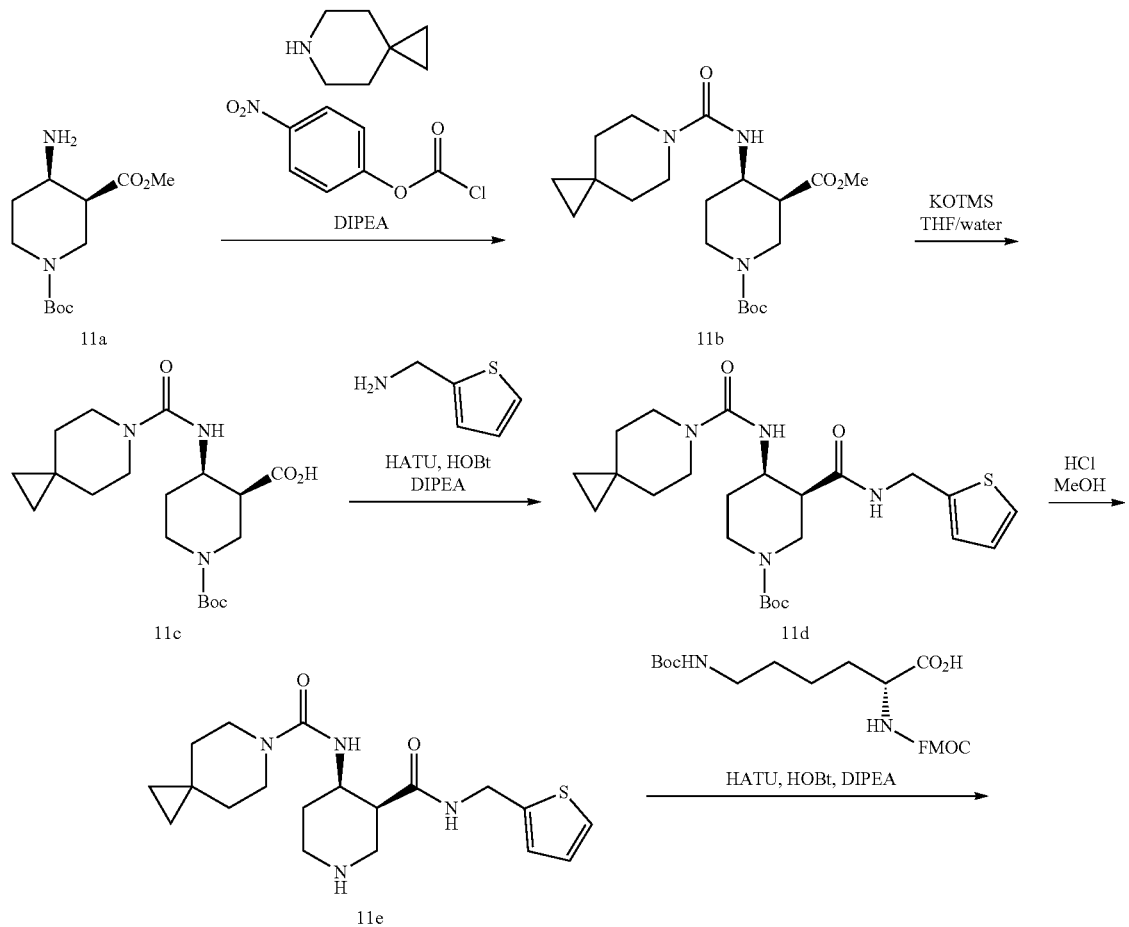

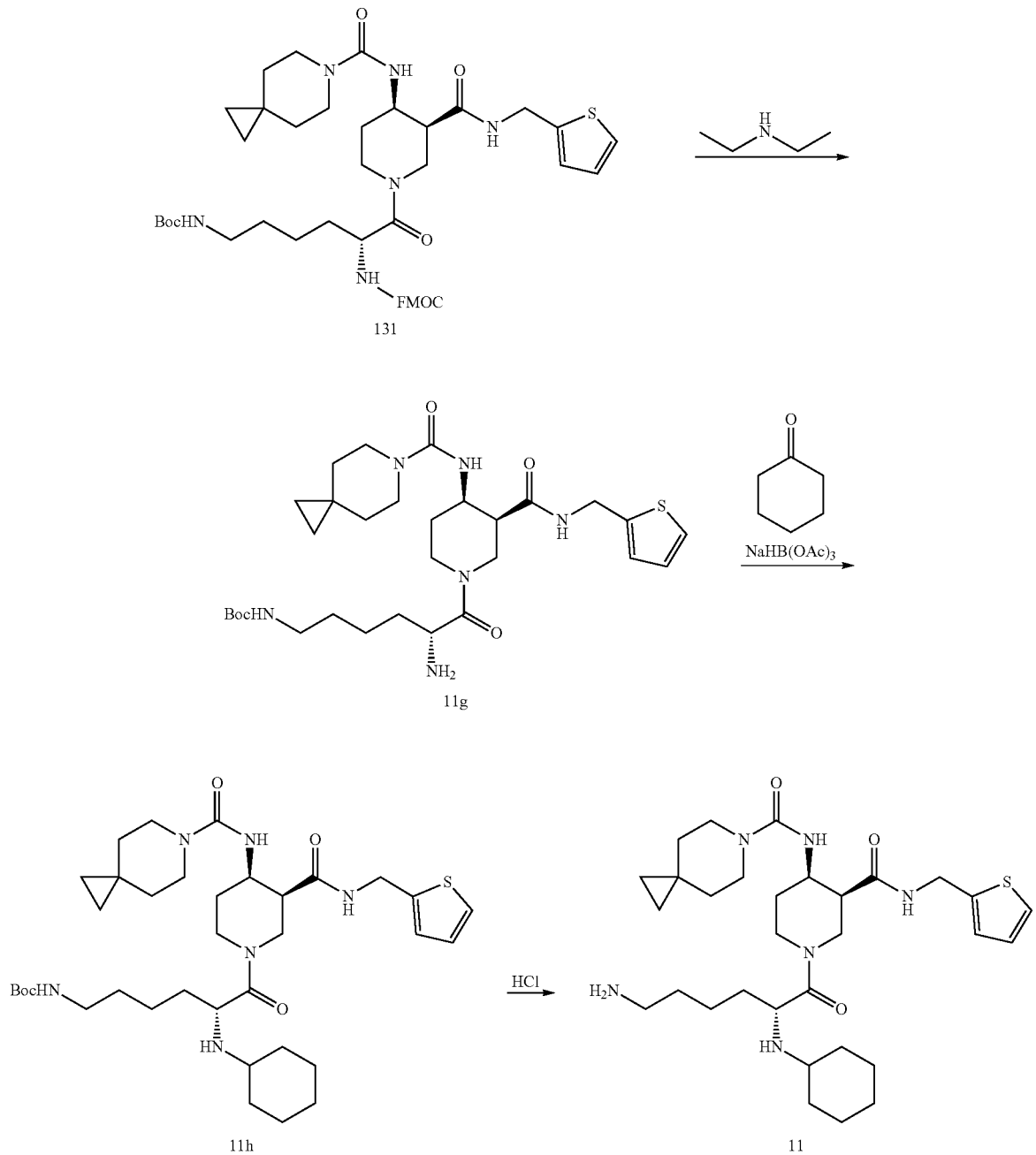

1-(tert-butyl) 3-methyl (3S,4R)-4-(6-azaspiro[2.5]octane-6-carboxamido)piperidine-1,3-dicarboxylate (11b)

To a 40 mL reaction vial was added (3S,4R)-1-tert-butyl 3-methyl 4-aminopiperidine-1,3-dicarboxylate (75 mg, 0.290 mmol), N-ethyl-N-isopropylpropan-2-amine (188 mg, 1.452 mmol), THF (2 ml) and DCM (1 ml). The reaction was cooled to 0° C. via an ice water bath. Then, 4-nitrophenyl carbonochloridate (61.4 mg, 0.305 mmol) was added. The reaction was warmed to room temp and stirred for 30 min. Then, a mixture of 6-azaspiro[2.5]octane (48.4 mg, 0.436 mmol) and N-ethyl-N-isopropylpropan-2-amine (113 mg, 0.871 mmol) in DCM (2 mL) was added to the reaction. The reaction stirred at room temp overnight. The reaction was concentrated and purified via ISCO (24 g column, 0-20% methanol/dichloromethane for 30 minutes). Fractions showing the product by LCMS were concentrated to provide 11b. LC-MS for 11b: calculated for $C_{20}H_{33}N_3O_5$ 395, observed m/e: 396 (M+H)$^+$; (Rt 1.11/2.0 min).

(3S,4R)-1-(tert-butoxycarbonyl)-4-(6-azaspiro[2.5]octane-6-carboxamido)piperidine-3-carboxylic acid (11c)

To a round bottom flask containing (3S,4R)-1-tert-butyl 3-methyl 4-(6-azaspiro[2.5]octane-6-carboxamido)piperidine-1,3-dicarboxylate (3.465 g, 8.76 mmol) was added water (45 ml), THF (30 ml)) and potassium trimethylsilanolate (3.415 g, 26.6 mmol) The round bottom was capped, and the reaction was allowed to stir at room temp for ~1 hr. The reaction was quenched with HCl (70.1 ml, 70.1 mmol), diluted with ethyl acetate, and the organic was extracted out (twice) and concentrated. The crude product was used directly in subsequent chemistry. LC-MS for 11c: calculated for $C_{19}H_{31}N_3O_5$ 381.2, observed m/e: 382.3 (M+H)$^+$; (Rt 0.92/2.0 min).

tert-butyl (3S,4R)-4-(6-azaspiro[2.5]octane-6-carboxamido)-3-((thiophen-2-ylmethyl)carbamoyl)piperidine-1-carboxylate (11d)

To a round bottom flask was added the following: (3S,4R)-1-(tert-butoxycarbonyl)-4-(6-azaspiro[2.5]octane-6-carboxamido)piperidine-3-carboxylic acid (500 mg, 1.311 mmol), thiophen-2-ylmethanamine (223 mg, 1.966 mmol), 1H-benzo[d][1,2,3]triazol-1-ol hydrate (301 mg, 1.966 mmol), DMF (8 ml), N-ethyl-N-isopropylpropan-2-amine (847 mg, 6.55 mmol) and 2-(3H-[1,2,3]triazolo[4,5-b]pyridin-3-yl)-1,1,3,3-tetramethylisouronium hexafluorophosphate(V) (748 mg, 1.966 mmol). The vial was capped, and the reaction was allowed to stir at room temp overnight. The reaction was diluted with water and ethyl acetate. The organic layer was extracted out (twice) and concentrated. The crude was purified via ISCO (120 g column, 0-20% methanol/dichloromethane, 30 minute run). The desired fraction were concentrated to provide 11d. LC-MS for 11d: calculated for $C_{24}H_{36}N_4O_4S$: 476.2, observed m/e: 477.3 (M+H)$^+$; (Rt 1.22/2.0 min).

N-((3S,4R)-3-((thiophen-2-ylmethyl)carbamoyl)piperidin-4-yl)-6-azaspiro[2.5]octane-6-carboxamide (11e)

To a round bottom flask containing (3S,4R)-tert-butyl 4-(6-azaspiro[2.5]octane-6-carboxamido)-3-((thiophen-2-ylmethyl)carbamoyl)piperidine-1-carboxylate (470 mg, 0.986 mmol) was added DCM (8 mL) and hydrogen chloride (8 mL, 32.0 mmol). The vial was capped, and the reaction stirred at room temp for 1 hr. The reaction was concentrated to provide 11e. LC-MS for 11e: calculated for $C_{19}H_{28}N_4O_2S$: 376.2, observed m/e: 377.3 (M+H)$^+$; (Rt 0.75/2.0 min).

(9H-fluoren-9-yl)methyl tert-butyl ((R)-6-((3S,4R)-4-(6-azaspiro[2.5]octane-6-carboxamido)-3-((thiophen-2-ylmethyl)carbamoyl)piperidin-1-yl)-6-oxohexane-1,5-diyl)dicarbamate (11f)

A mixture of N-((3S,4R)-3-((thiophen-2-ylmethyl)carbamoyl)piperidin-4-yl)-6-azaspiro[2.5]octane-6-carboxamide (257 mg, 0.622 mmol), (R)-2-((((9H-fluoren-9-yl)methoxy)carbonyl)amino)-6-((tert-butoxycarbonyl)amino)hexanoic acid (321 mg, 0.685 mmol), HATU (284 mg, 0.747 mmol), and TEA (0.347 ml, 2.489 mmol) in THF (3 ml) was stirred at RT for 3 hours. It was quenched with saturated sodium bicarbonate, filtered, and extracted with EtOAc. The organics were dried with MgSO$_4$ and concentrated to residue. It was loaded on RediSep 12 g eluting with 0-75% EtOAc:EtOH (3:1)/hexanes as concentrate to provide 11f. LC-MS for 11f: calculated for $C_{45}H_{58}N_6O_7S$ 826.4, observed m/e: 827.4 (M+H)$^+$: (Rt 1.48/2.0 min).

tert-butyl ((R)-6-((3S,4R)-4-(6-azaspiro[2.5]octane-6-carboxamido)-3-((thiophen-2-ylmethyl)carbamoyl)piperidin-1-yl)-5-amino-6-oxohexyl)carbamate (11g)

A solution of (9H-fluoren-9-yl)methyl tert-butyl ((R)-6-((3S,4R)-4-(6-azaspiro[2.5]octane-6-carboxamido)-3-((thiophen-2-ylmethyl)carbamoyl)piperidin-1-yl)-6-oxohexane-1,5-diyl)dicarbamate (342 mg, 0.414 mmol) in THF (2 ml) was added diethylamine (0.4 ml, 3.83 mmol). The reaction was stirred at RT overnight and concentrated to residue. The crude material was used in next step without further purification. LC-MS for 11g: calculated for $C_{30}H_{48}N_6O_5S$: 604.3, observed m/e: 605.5 (M+H)$^+$; (Rt 1.00/2.0 min).

tert-butyl ((R)-6-((3S,4R)-4-(6-azaspiro[2.5]octane-6-carboxamido)-3-((thiophen-2-ylmethyl)carbamoyl)piperidin-1-yl)-5-(cyclohexylamino)-6-oxohexyl)carbamate (11h)

Cyclohexanone (1.74 g, 17.71 mmol) was added to tert-butyl ((R)-6-((3S,4R)-4-(6-azaspiro[2.5]octane-6-carboxamido)-3-((thiophen-2-ylmethyl)carbamoyl)piperidin-1-yl)-5-amino-6-oxohexyl)carbamate (3.57 g, 17.71 mmol) in 40 mL of DCE. Sodium triacetoxyborohydride (5 g, 23.61 mmol) was then added to the solution, and it was stirred for 1 hr at room temperature. The reaction was quenched with H$_2$O and extracted with DCM.

The organic layer was dried with MgSO$_4$, filtered, and concentrated. The residue was purified by column chromatography on silica gel Teledyne Isco RediSep[80 g pre-packed] eluting with 0% EtOAc/EtOH=3/1 to 100% in hexanes to give 11h. LC-MS for 11h: calculated for $C_{36}H_{58}N_6O_5S$ 686.4, observed m/e: 687.7 (M+H)$^+$; (Rt 1.09/2.0 min).

N-((3S,4R)-1-(cyclo hexyl-D-lysyl)-3-((thiophen-2-ylmethyl)carbamoyl)piperidin-4-yl)-6-azaspiro[2.5]octane-6-carboxamide (11)

tert-butyl ((R)-6-((3S,4R)-4-(6-azaspiro[2.5]octane-6-carboxamido)-3-((thiophen-2-ylmethyl)carbamoyl)piperidin-11-yl)-5-(cyclohexylamino)-6-oxohexyl)carbamate (56 mg, 0.082 mmol) was dissolved in MeOH (0.5 ml) and HCl (0.204 ml, 0.815 mmol) in dioxane was added. It was stirred at room temperature for 2 hours. The mixture was concentrated to a residue and purified by reverse phase HPLC to provide 11. LC-MS for 11: calculated for $C_{31}H_{50}N_6O_3S$ 586.4, observed m/e: 587.5 (M+H)$^+$; (Rt 0.87/2.0 min).

By using the procedures similar to those described above, and appropriate starting materials, the following compounds were synthesized.

| Compound Number | Structure | Name | Exact Mass [M + H]+ | FXIIa IC50 (nM) |
| --- | --- | --- | --- | --- |
| 11 | 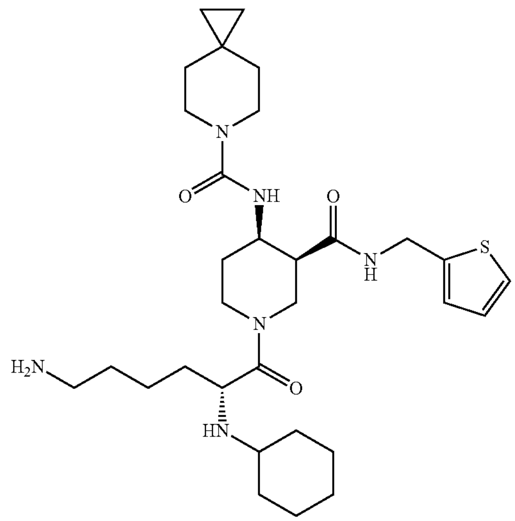 [SMILES: NCCCC[C@@H](NC1CCCCC1)C(=O)N1CC[C@@H](NC(=O)N2CCC3(CC2)CC3)[C@@H](C(=O)NCc2cccs2)C1] | N-{(3S,4R)-1-(N~2~-cyclohexyl-D-lysyl)-3-[(thiophen-2-ylmethyl)carbamoyl]piperidin-4-yl}-6-azaspiro[2.5]octane-6-carboxamide | 587 | 71.6 |
| 12 | 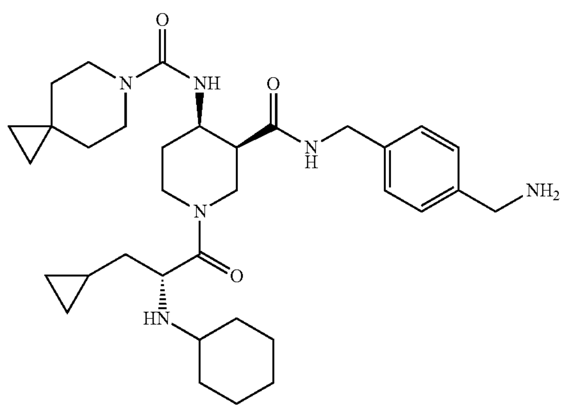 [SMILES: NCc1ccc(CNC(=O)[C@H]2CN(C(=O)[C@@H](CC3CC3)NC3CCCCC3)CC[C@H]2NC(=O)N2CCC3(CC2)CC3)cc1] | N-[(3S,4R)-3-{[4-(aminomethyl)benzyl]carbamoyl}-1-(N-cyclohexyl-3-cyclopropyl-D-alanyl)piperidin-4-yl]-6-azaspiro[2.5]octane-6-carboxamide | 593 | 41.7 |
| 13 | 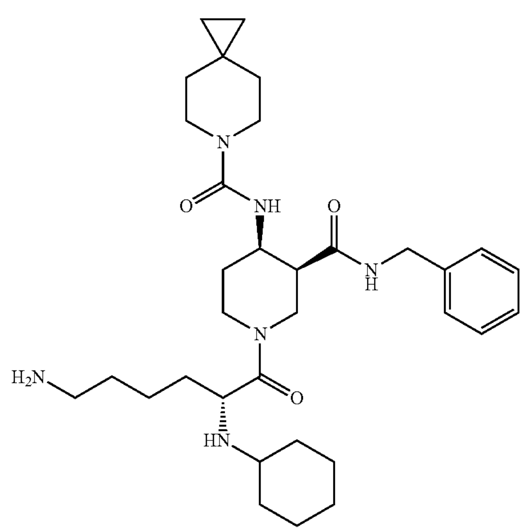 [SMILES: NCCCC[C@@H](NC1CCCCC1)C(=O)N1CC[C@@H](NC(=O)N2CCC3(CC2)CC3)[C@@H](C(=O)NCc2ccccc2)C1] | N-[(3S,4R)-3-(benzylcarbamoyl)-1-(N~2~-cyclohexyl-D-lysyl)piperidin-4-yl]-6-azaspiro[2.5]octane-6-carboxamide | 581 | 98.3 |

-continued

| Compound Number | Structure | Name | Exact Mass [M + H]+ | FXIIa IC50 (nM) |
|---|---|---|---|---|
| 14 | 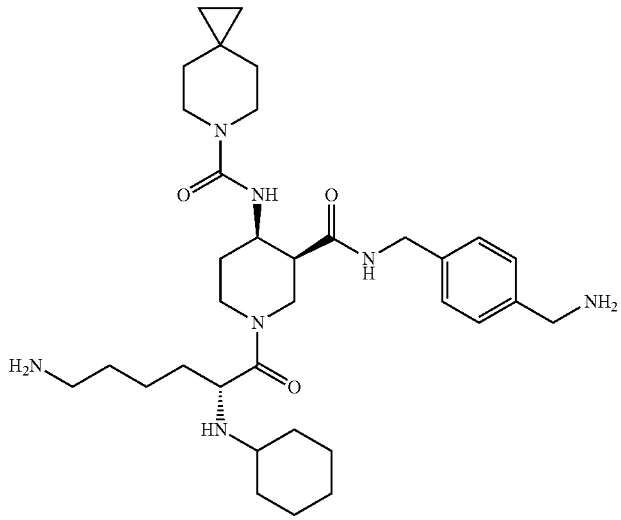 [SMILES: NCCCC[C@@H](NC1CCCCC1)C(=O)N1CC[C@@H](NC(=O)N2CCC3(CC2)CC3)[C@@H](C(=O)NCc2ccc(CN)cc2)C1] | N-[(3S,4R)-3-{[4-(aminomethyl)benzyl]carbamoyl}-1-(N~2~-cyclohexyl-D-lysyl)piperidin-4-yl]-6-azaspiro[2.5]octane-6-carboxamide | 610 | 18.7 |
| 15 | 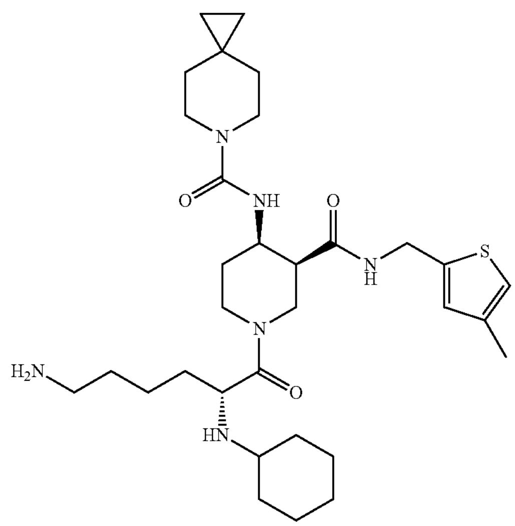 [SMILES: Cc1csc(CNC(=O)[C@H]2CN(C(=O)[C@@H](CCCCN)NC3CCCCC3)CC[C@H]2NC(=O)N2CCC3(CC2)CC3)c1] | N-[(3S,4R)-1-(N~2~-cyclohexyl-D-lysyl)-3-{[(4-methylthiophen-2-yl)methyl]carbamoyl}piperidin-4-yl]-6-azaspiro[2.5]octane-6-carboxamide | 601 | 60.2 |
| 16 | 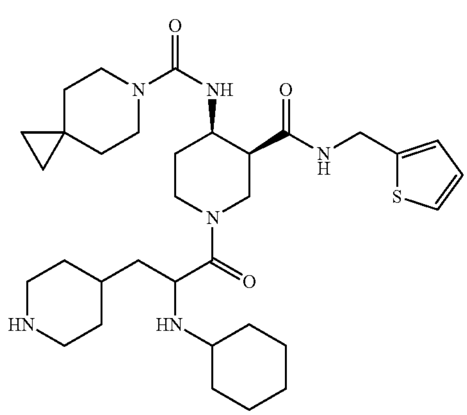 [SMILES: O=C(NCc1cccs1)[C@H]1CN(C(=O)C(CC2CCNCC2)NC2CCCCC2)CC[C@H]1NC(=O)N1CCC2(CC1)CC2] | N-{(3S,4R)-1-(N-cyclohexyl-3-piperidin-4-ylalanyl)-3-[(thiophen-2-ylmethyl)carbamoyl]piperidin-4-yl}-6-azaspiro[2.5]octane-6-carboxamide | 616 | 82.9 |

-continued

| Compound Number | Structure | Name | Exact Mass [M + H]+ | FXIIa IC50 (nM) |
|---|---|---|---|---|
| 17 | 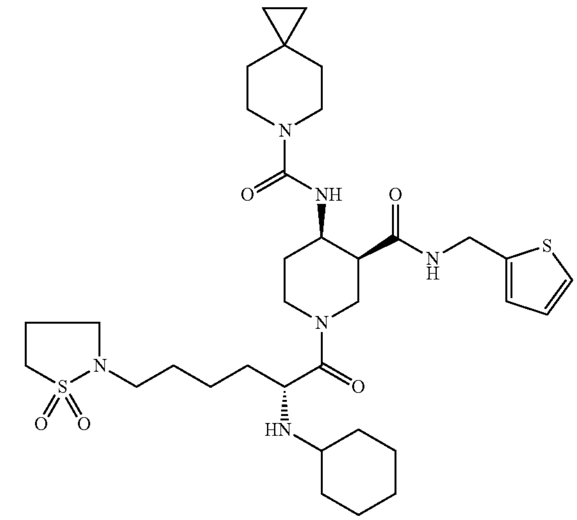 [SMILES: O=C(NCc1cccs1)[C@H]1CN(C(=O)[C@@H](CCCCN2CCCS2(=O)=O)NC2CCCCC2)CC[C@H]1NC(=O)N1CCC2(CC1)CC2] | N-{(3S,4R)-1-[N-cyclohexyl-6-(1,1-dioxidoisothiazolidin-2-yl)-D-norleucyl]-3-[(thiophen-2-ylmethyl)carbamoyl]piperidin-4-yl}-6-azaspiro[2.5]octane-6-carboxamide | 691 | 11.5 |
| 18 | 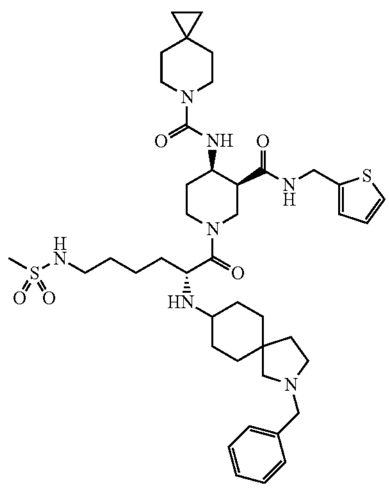 [SMILES: CS(=O)(=O)NCCCC[C@@H](NC1CCC2(CC1)CCN(Cc1ccccc1)C2)C(=O)N1CC[C@@H](NC(=O)N2CCC3(CC2)CC3)[C@@H](C(=O)NCc2cccs2)C1] | N-{(3S,4R)-1-[N~2~-(2-benzyl-2-azaspiro[4.5]dec-8-yl)-N~6~-(methylsulfonyl)-D-lysyl]-3-[(thiophen-2-ylmethyl)carbamoyl]piperidin-4-yl}-6-azaspiro[2.5]octane-6-carboxamide | 810 | 29.2 |
| 19 | 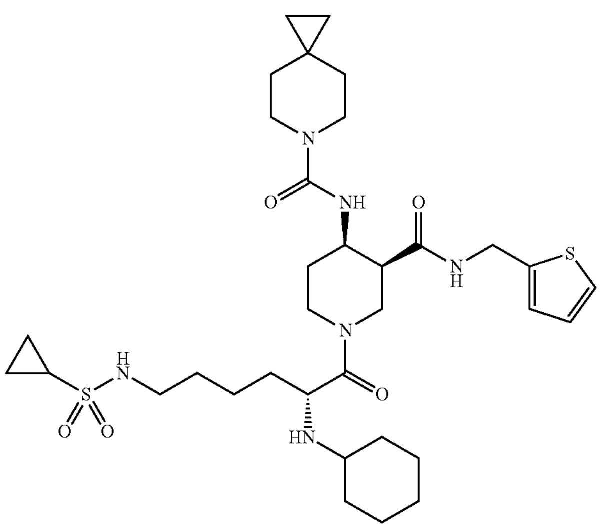 [SMILES: O=C(NCc1cccs1)[C@H]1CN(C(=O)[C@@H](CCCCNS(=O)(=O)C2CC2)NC2CCCCC2)CC[C@H]1NC(=O)N1CCC2(CC1)CC2] | N-{(3S,4R)-1-[N~2~-cyclohexyl-N~6~-(cyclopropylsulfonyl)-D-lysyl]-3-[(thiophen-2-ylmethyl)carbamoyl]piperidin-4-yl}-6-azaspiro[2.5]octane-6-carboxamide | 691 | 43.1 |

-continued

| Compound Number | Structure | Name | Exact Mass [M + H]+ | FXIIa IC50 (nM) |
|---|---|---|---|---|
| 20 | 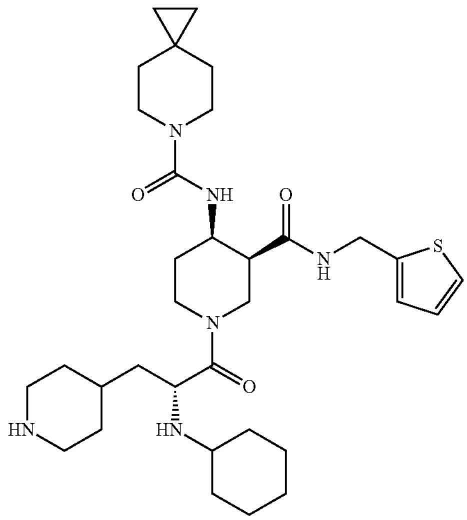 [SMILES: O=C(NCc1cccs1)[C@H]1CN(C(=O)[C@@H](CC2CCNCC2)NC2CCCCC2)CC[C@H]1NC(=O)N1CCC2(CC1)CC2] | N-{(3S,4R)-1-(N-cyclohexyl-3-piperidin-4-yl-D-alanyl)-3-[(thiophen-2-ylmethyl)carbamoyl]piperidin-4-yl}-6-azaspiro[2.5]octane-6-carboxamide | 613 | 47.2 |
| 21 | 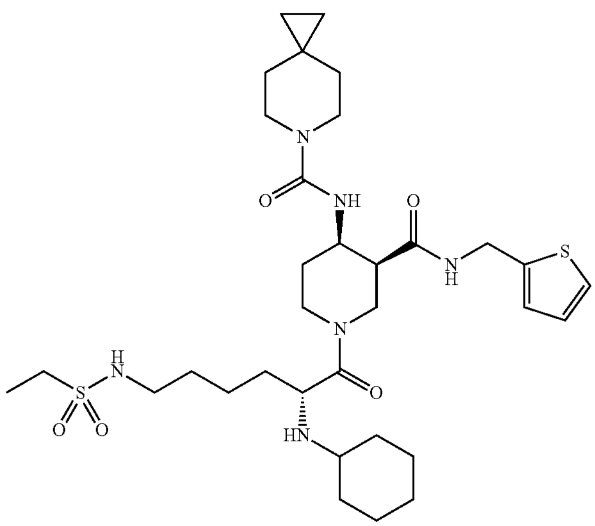 [SMILES: CCS(=O)(=O)NCCCC[C@@H](NC1CCCCC1)C(=O)N1CC[C@@H](NC(=O)N2CCC3(CC2)CC3)[C@@H](C(=O)NCc2cccs2)C1] | N-{(3S,4R)-1-[N~2~-cyclohexyl-N~6~-(ethylsulfonyl)-D-lysyl]-3-[(thiophen-2-ylmethyl)carbamoyl]piperidin-4-yl}-6-azaspiro[2.5]octane-6-carboxamide | 679 | 51.2 |
| 22 | 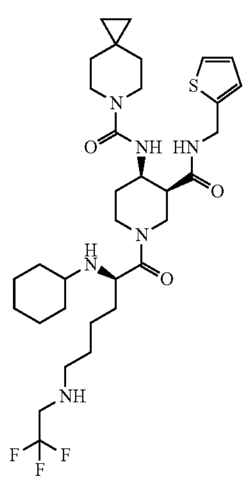 [SMILES: O=C(NCc1cccs1)[C@H]1CN(C(=O)[C@@H](CCCCNCC(F)(F)F)NC2CCCCC2)CC[C@H]1NC(=O)N1CCC2(CC1)CC2] | N-{(3S,4R)-1-[N~2~-cyclohexyl-N~6~-(2,2,2-trifluoroethyl)-D-lysyl]-3-[(thiophen-2-ylmethyl)carbamoyl]piperidin-4-yl}-6-azaspiro[2.5]octane-6-carboxamide | 669 | 46.5 |

-continued

| Compound Number | Structure | Name | Exact Mass [M + H]+ | FXIIa IC50 (nM) |
|---|---|---|---|---|
| 23 | 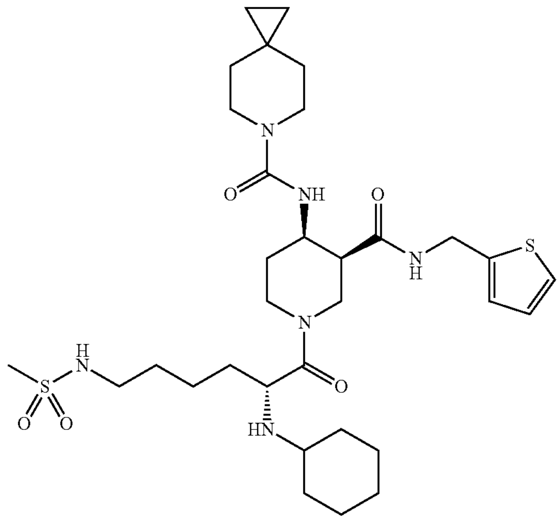 [SMILES: CS(=O)(=O)NCCCC[C@@H](NC1CCCCC1)C(=O)N1CC[C@@H](NC(=O)N2CCC3(CC2)CC3)[C@@H](C(=O)NCc2cccs2)C1] | N-{(3S,4R)-1-[N~2~-cyclohexyl-N~6~-(methylsulfonyl)-D-lysyl]-3-[(thiophen-2-ylmethyl)carbamoyl]piperidin-4-yl}-6-azaspiro[2.5]octane-6-carboxamide | 665 | 52.4 |
| 24 | 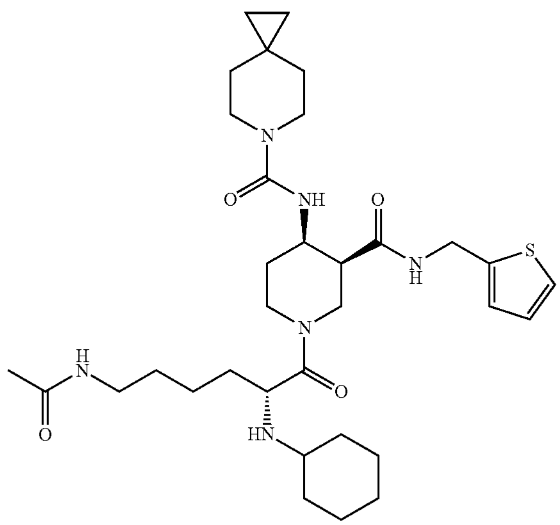 [SMILES: CC(=O)NCCCC[C@@H](NC1CCCCC1)C(=O)N1CC[C@@H](NC(=O)N2CCC3(CC2)CC3)[C@@H](C(=O)NCc2cccs2)C1] | N-{(3S,4R)-1-(N~6~-acetyl-N~2~-cyclohexyl-D-lysyl)-3-[(thiophen-2-ylmethyl)carbamoyl]piperidin-4-yl}-6-azaspiro[2.5]octane-6-carboxamide | 629 | 108.4 |
| 25 | 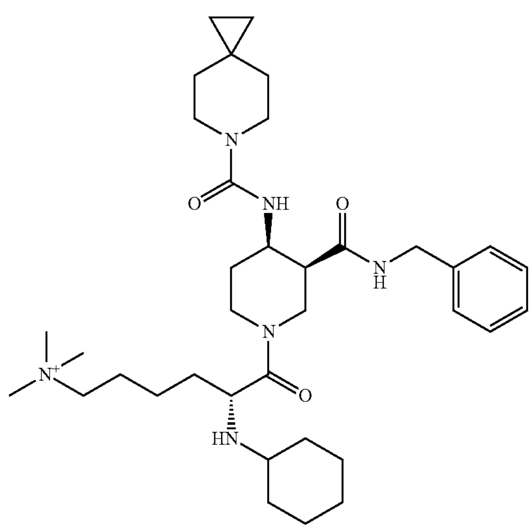 [SMILES: C[N+](C)(C)CCCC[C@@H](NC1CCCCC1)C(=O)N1CC[C@@H](NC(=O)N2CCC3(CC2)CC3)[C@@H](C(=O)NCc2ccccc2)C1] | (5R)-6-[(3S,4R)-4-[(6-azaspiro[2.5]oct-6-ylcarbonyl)amino]-3-(benzylcarbamoyl)piperidin-1-yl]-5-(cyclohexylamino)-N,N,N-trimethyl-6-oxohexan-1-aminium | 623 | 5.0 |

-continued

| Compound Number | Structure | Name | Exact Mass [M + H]+ | FXIIa IC50 (nM) |
|---|---|---|---|---|
| 26 | 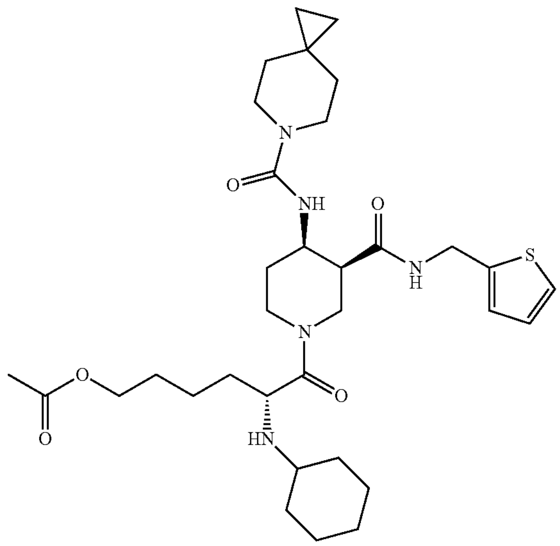 [SMILES: CC(=O)OCCCC[C@@H](NC1CCCCC1)C(=O)N1CC[C@@H](NC(=O)N2CCC3(CC2)CC3)[C@@H](C(=O)NCc2cccs2)C1] | (5R)-6-{(3S,4R)-4-[(6-azaspiro[2.5]oct-6-ylcarbonyl)amino]-3-[(thiophen-2-ylmethy)carbamoyl]piperidin-1-yl}-5-(cyclohexylamino)-6-oxohexyl acetate | 630 | 65.9 |
| 27 | 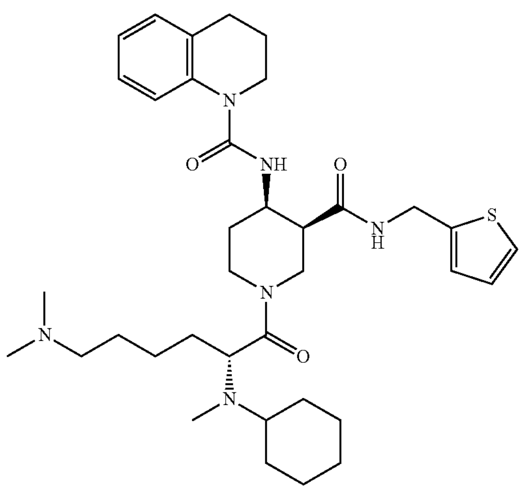 [SMILES: CN(C)CCCC[C@H](C(=O)N1CC[C@@H](NC(=O)N2CCCc3ccccc32)[C@@H](C(=O)NCc2cccs2)C1)N(C)C1CCCCC1] | N-{(3S,4R)-1-(N~2~-cyclohexyl-N~2~,N~6~,N~6~-trimethyl-D-lysyl)-3-[(thiophen-2-ylmethyl)carbamoyl]piperidin-4-yl}-3,4-dihydroquinoline-1(2H)-carboxamide | 651 | 110.4 |
| 28 | 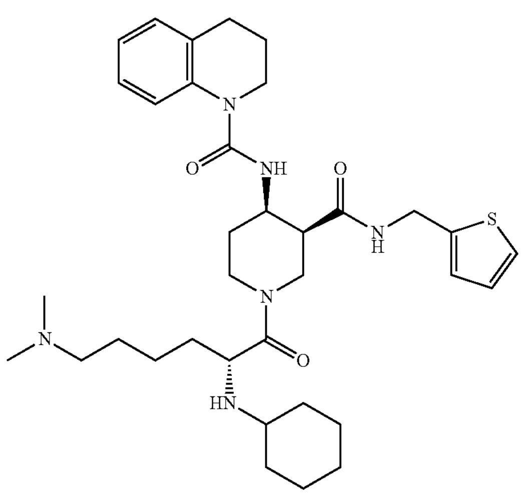 [SMILES: CN(C)CCCC[C@@H](NC1CCCCC1)C(=O)N1CC[C@@H](NC(=O)N2CCCc3ccccc32)[C@@H](C(=O)NCc2cccs2)C1] | N-{(3S,4R)-1-(N~2~-cyclohexyl-N~6~,N~6~-dimethyl-D-lysyl)-3-[(thiophen-2-ylmethyl)carbamoyl]piperidin-4-yl}-3,4-dihydroquinoline-1(2H)-carboxamide | 637 | 101.9 |

-continued

| Compound Number | Structure | Name | Exact Mass [M + H]+ | FXIIa IC50 (nM) |
|---|---|---|---|---|
| 29 | 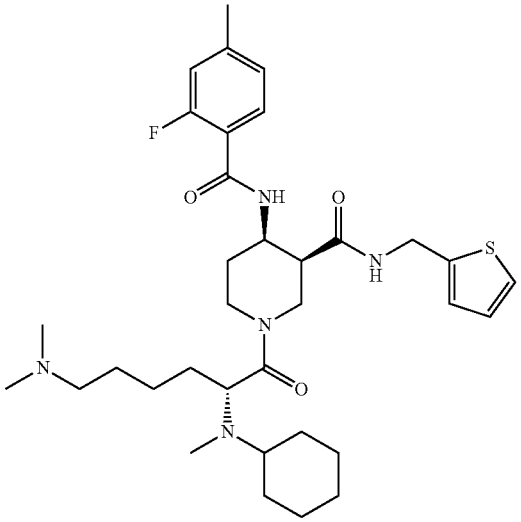 [SMILES: Cc1ccc(C(=O)N[C@@H]2CCN(C(=O)[C@@H](CCCCN(C)C)N(C)C3CCCCC3)C[C@@H]2C(=O)NCc2cccs2)c(F)c1] | (3S,4R)-1-(N~2~-cyclohexyl-N~2~,N~6~,N~6~-trimethyl-D-lysyl)-4-{[(2-fluoro-4-methyl-phenyl)carbonyl]amino}-N-(thiophen-2-ylmethyl)piperidine-3-carboxamide | 628 | 37.6 |
| 30 | 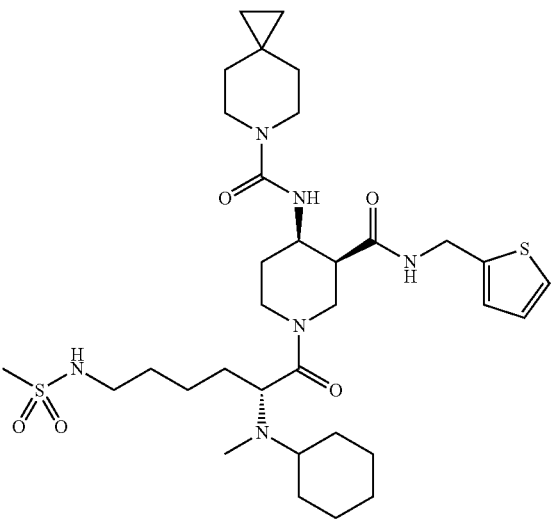 [SMILES: CN(C1CCCCC1)[C@H](CCCCNS(C)(=O)=O)C(=O)N1CC[C@@H](NC(=O)N2CCC3(CC2)CC3)[C@@H](C(=O)NCc2cccs2)C1] | N-{(3S,4R)-1-[N~2~-cyclohexyl-N~2~-methyl-N~6~-(methylsulfonyl)-D-lysyl]-3-[(thiophen-2-ylmethyl)carbamoyl]piperidin-4-yl}-6-azaspiro[2.5]octane-6-carboxamide | 679 | 50.1 |
| 31 | 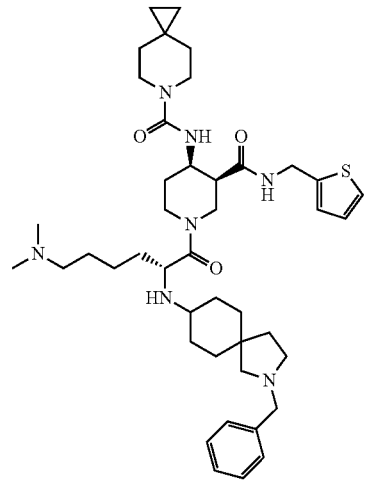 [SMILES: CN(C)CCCC[C@@H](NC1CCC2(CC1)CCN(Cc1ccccc1)C2)C(=O)N1CC[C@@H](NC(=O)N2CCC3(CC2)CC3)[C@@H](C(=O)NCc2cccs2)C1] | N-{(3S,4R)-1-[N~2~-(2-benzyl-2-azaspiro[4.5]dec-8-yl)-N~6~,N~6~-dimethyl-D-lysyl]-3-[(thiophen-2-ylmethyl)carbamoyl]piperidin-4-yl}-6-azaspiro[2.5]octane-6-carboxamide | 760 | 1.5 |

-continued

| Compound Number | Structure | Name | Exact Mass [M + H]+ | FXIIa IC50 (nM) |
|---|---|---|---|---|
| 32 | 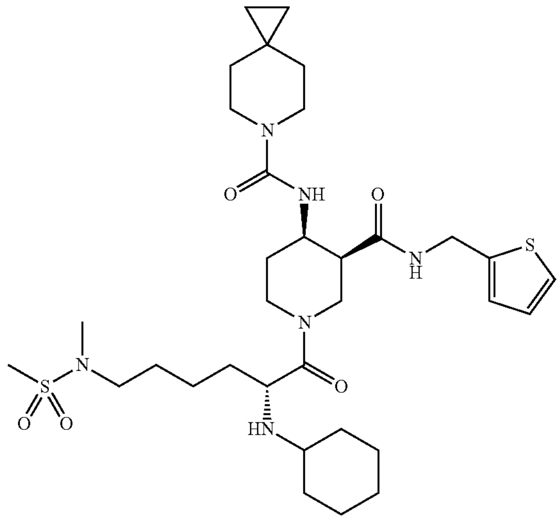 [SMILES: CN(CCCC[C@@H](NC1CCCCC1)C(=O)N1CC[C@@H](NC(=O)N2CCC3(CC2)CC3)[C@@H](C(=O)NCc2cccs2)C1)S(C)(=O)=O] | N-{(3S,4R)-1-[N~2~-cyclohexyl-N~6~-methyl-N~6~-(methylsulfonyl)-D-lysyl]-3-[(thiophen-2-ylmethyl)carbamoyl]piperidin-4-yl}-6-azaspiro[2.5]octane-6-carboxamide | 679 | 22.5 |
| 33 | 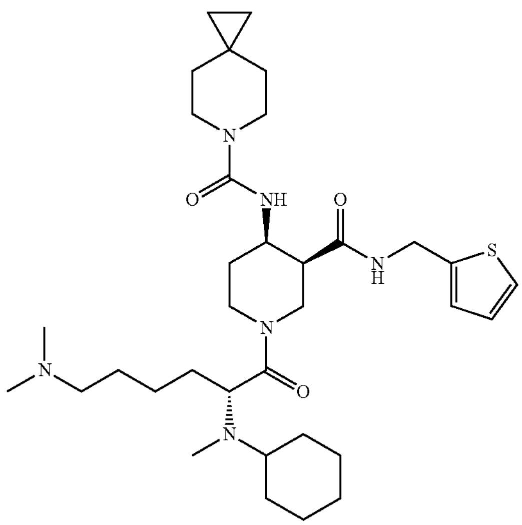 [SMILES: CN(C)CCCC[C@H](C(=O)N1CC[C@@H](NC(=O)N2CCC3(CC2)CC3)[C@@H](C(=O)NCc2cccs2)C1)N(C)C1CCCCC1] | N-{(3S,4R)-1-(N~2~-cyclohexyl-N~2~,N~6~,N~6~-trimethyl-D-lysyl)-3-[(thiophen-2-ylmethyl)carbamoyl]piperidin-4-yl}-6-azaspiro[2.5]octane-6-carboxamide | 629 | 15.1 |
| 34 | 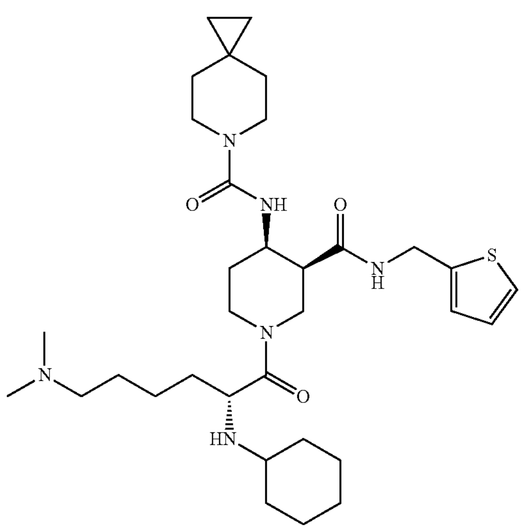 [SMILES: CN(C)CCCC[C@@H](NC1CCCCC1)C(=O)N1CC[C@@H](NC(=O)N2CCC3(CC2)CC3)[C@@H](C(=O)NCc2cccs2)C1] | N-{(3S,4R)-1-(N~2~-cyclohexyl-N~6~,N~6~-dimethyl-D-lysyl)-3-[(thiophen-2-ylmethyl)carbamoyl]piperidin-4-yl}-6-azaspiro[2.5]octane-6-carboxamide | 615 | 5.7 |

| Compound Number | Structure | Name | Exact Mass [M + H]+ | FXIIa IC50 (nM) |
| --- | --- | --- | --- | --- |
| 35 | 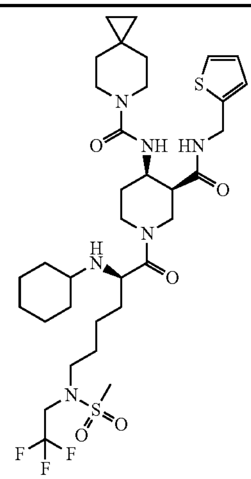 | N-{(3S,4R)-1-[N~2~-cyclohexyl-N~6~-(methylsulfonyl)-N~6~-(2,2,2-trifluoroethyl)-D-lysyl]-3-[(thiophen-2-ylmethyl)carbamoyl]piperidin-4-yl}-6-azaspiro[2.5]octane-6-carboxamide | 747 | 19.5 |
| 36 | | N-((3S,4R)-1-((R)-3-cyclohexyl-2-(cyclohexylamino)propanoyl)-3-((thiophen-2-ylmethyl)carbamoyl)piperidin-4-yl)-1-oxo-2,7-diazaspiro[4.5]decane-7-carboxamide | 650 | 428.5 |

Factor XIIa assay

The effectiveness of a compound of the present invention as an inhibitor of Coagulation Factor XIIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the IC50, the inhibitor concentration causing a 50% decrease in Factor XIIa protease activity.

Factor XIIa activity determinations were made in 50 mM HEPES buffer containing 150 mM NaCl, 5 mM $CaCl_2$, and 0.1% PEG 8000 (polyethylene glycol; JT Baker or Fisher Scientific) at pH 7.4. Determinations were made using purified human Factor XIIa at a final concentration of 500 µM (Sekisui Diagnostics) and the synthetic substrate, n-Acetyl-Lys-Pro-Arg-AFC, TFA salt (Sigma # C6608) at a concentration of 100 µM.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. IC50 was determined as the concentration of 1 yielding $V_i = V_o/2$.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

What is claimed is:
1. A compound of the formula:

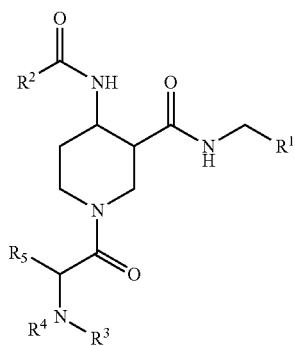

wherein $R^1$ is aryl or heteroaryl, wherein said aryl and heteroaryl groups are optionally substituted with one to three substituents independently selected from the group consisting of hydroxyl, cyano, halo, $C_{1-3}$ alkyl, $O(C_{1-3}$ alkyl), $NH_2$, $CH_2NH_2$, $(C=O)NH_2$ or heteroaryl;

$R^2$ is aryl, heteroaryl,

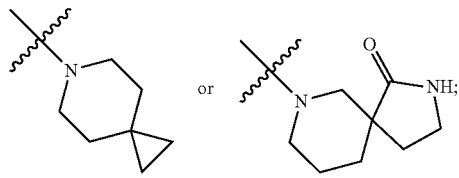 [SMILES: *N1CCC2(CC1)CC2 ; *N1CCCC2(CCNC2=O)C1]

wherein said aryl and heteroaryl groups are optionally substituted with one to three substituents independently selected from the group consisting of hydroxyl, oxo, cyano, halo, $C_{1-3}$ alkyl, $C_{1-3}$ haloalkyl, $O(C_{1-3}$ alkyl) and $NH_2$;

$R^3$ is hydrogen, $C_{1-3}$ alkyl,

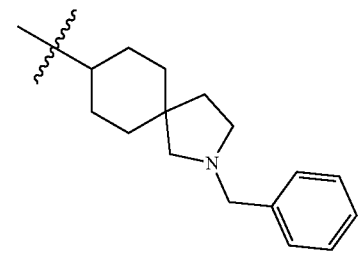 [SMILES: *C1CCC2(CC1)CCN(Cc1ccccc1)C2]

or $C_{3-7}$ cycloalkyl;

$R^4$ is hydrogen or $C_{1-4}$ alkyl;

$R^5$ is (a) hydrogen, (b) $CH_2$—$C_{3-6}$ cycloalkyl;

(c) piperidinyl, which is optionally substituted with hydroxyl, oxo, cyano, halo or $C_{1-3}$ alkyl, or (d) $C_{1-4}$ alkyl which is optionally substituted with $NR^6R^7$, $N^+(CH_3)_3$, $NH(C=O)R^6$, $O(C=O)R^6$, $NR^6SO_2R^7$, $NHSO_2$cyclopropyl or heterocyclyl, wherein said heterocyclyl is optionally substituted with $R^6$;

$R^6$ is hydrogen or $C_{1-4}$ alkyl, which is optionally substituted with one to three substituents independently selected from the group consisting of halo and hydroxyl;

$R^7$ is hydrogen or $C_{1-3}$ alkyl, which is optionally substituted with one to three substituents independently selected from the group consisting of halo and hydroxyl;

or a pharmaceutically acceptable salt thereof.

2. The compound of claim 1 wherein $R_1$ is indolyl, phenyl or thiazolyl, wherein said groups are optionally substituted with one to three substituents independently selected from the group consisting of halo, $C_{1-3}$ alkyl, $NH_2$, and $CH_2NH_2$, $(C=O)NH_2$; or a pharmaceutically acceptable salt thereof.

3. The compound of claim 2 wherein $R_1$ is thiazolyl, which is optionally substituted with $C_{1-3}$ alkyl, or a pharmaceutically acceptable salt thereof.

4. The compound of claim 1 wherein $R^2$ is thiazolyl, phenyl, dihydroquinolinyl,

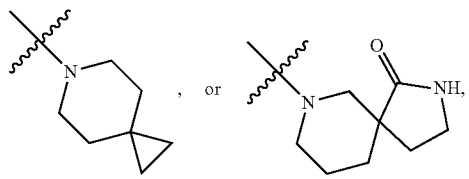 [SMILES: *N1CCC2(CC1)CC2 ; *N1CCCC2(CCNC2=O)C1]

wherein said thiazolyl and phenyl, groups are optionally substituted with one to three substituents independently selected from the group consisting of halo and $C_{1-3}$ alkyl; or a pharmaceutically acceptable salt thereof.

5. The compound of claim 1 wherein $R^3$ is cyclohexyl or

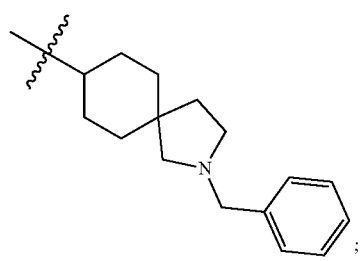 [SMILES: *C1CCC2(CC1)CCN(Cc1ccccc1)C2]

or a pharmaceutically acceptable salt thereof.

6. The compound of claim 1 wherein $R^4$ is hydrogen or methyl, or a pharmaceutically acceptable salt thereof.

7. The compound of claim 1 wherein $R^5$ is $C_{1-4}$ alkyl which is optionally substituted with $NR^6R^7$, $NH(C=O)R^6$, $NHSO_2R^7$, $NHSO_2$cyclopropyl or heterocyclyl, wherein said heterocyclyl is optionally substituted with $R^7$; or a pharmaceutically acceptable salt thereof.

8. A compound selected from

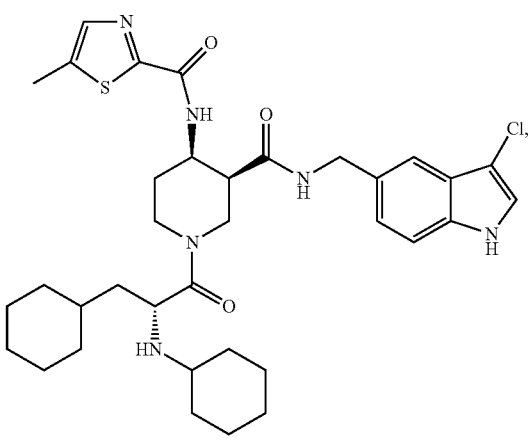

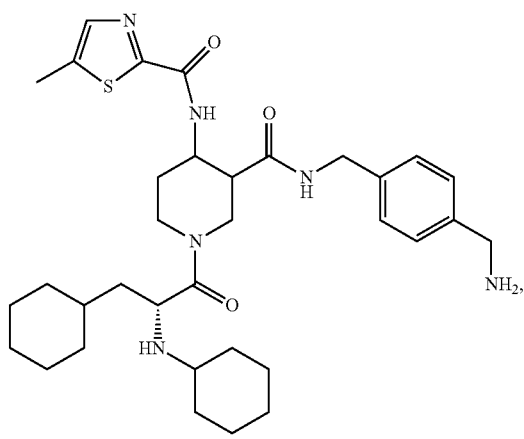
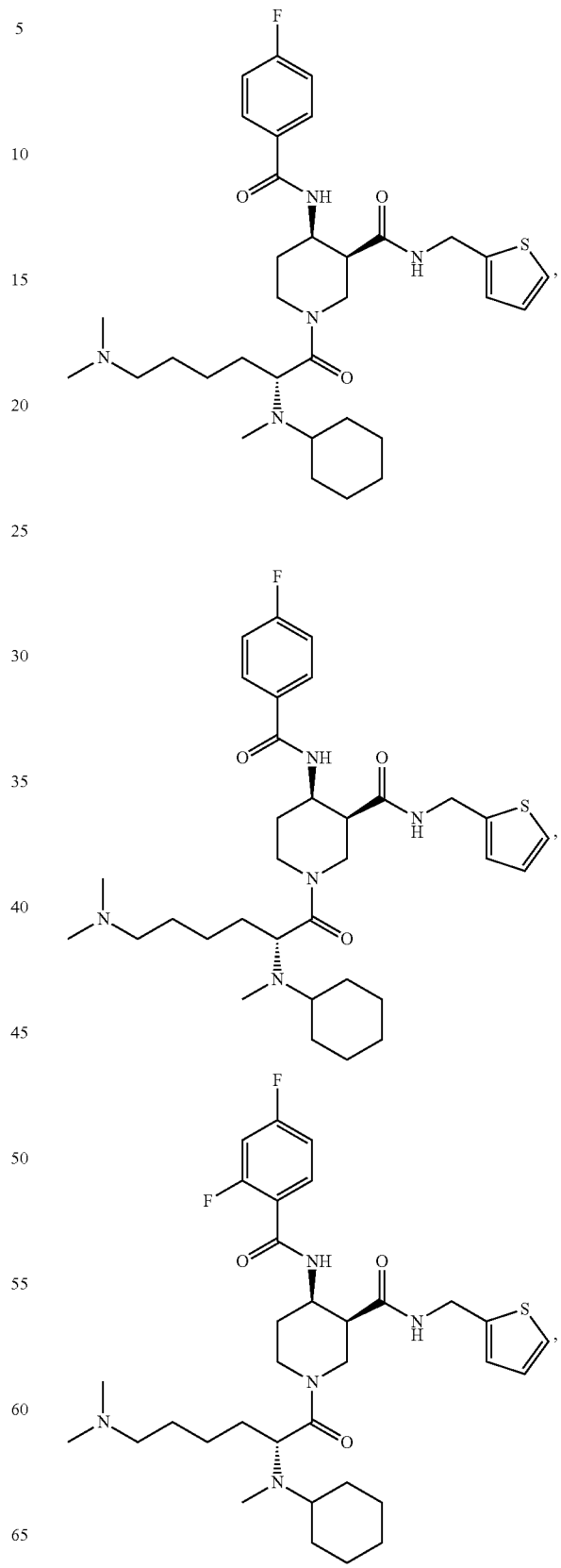

63
64
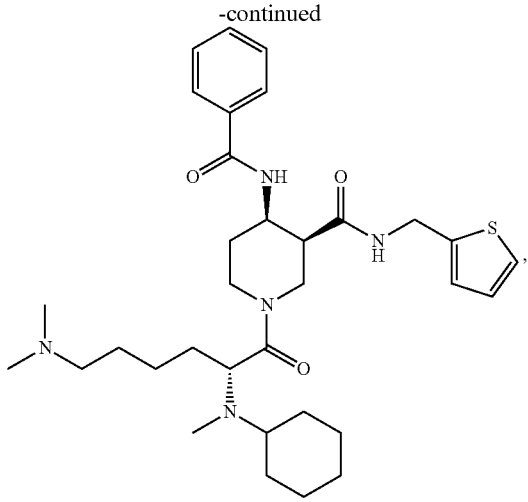
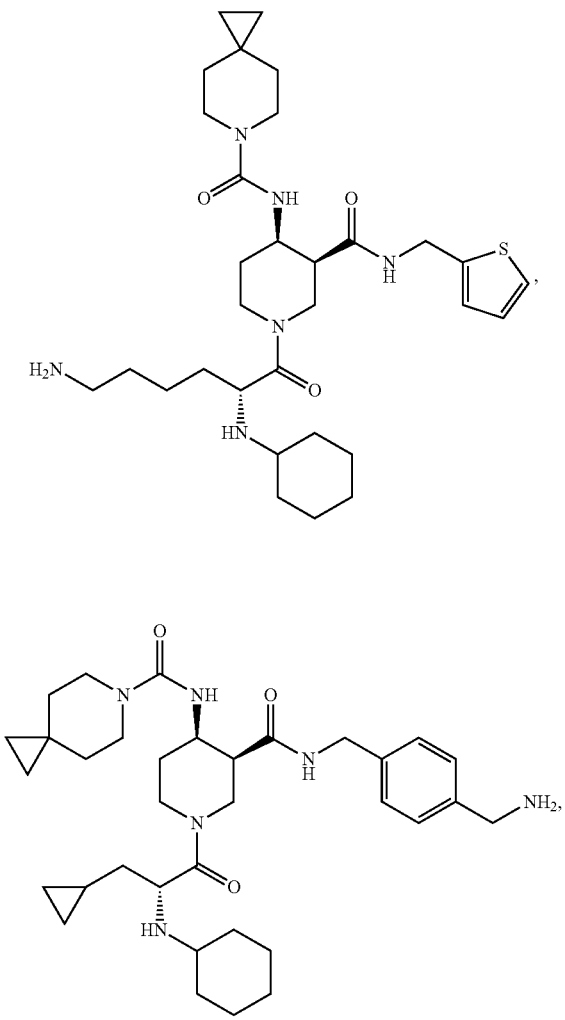
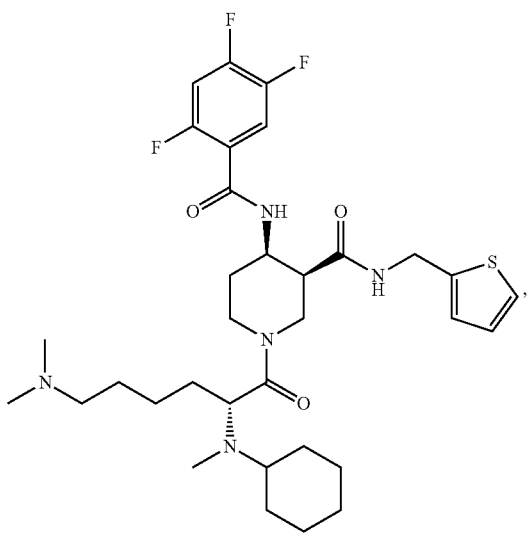
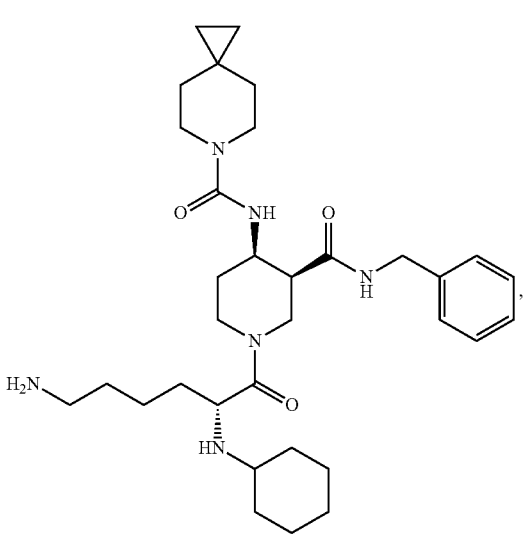

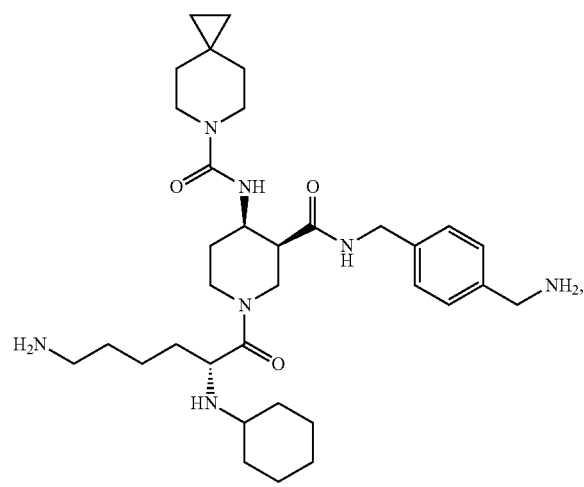
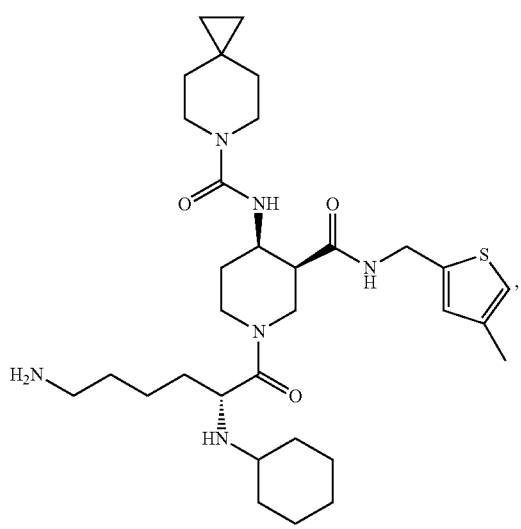
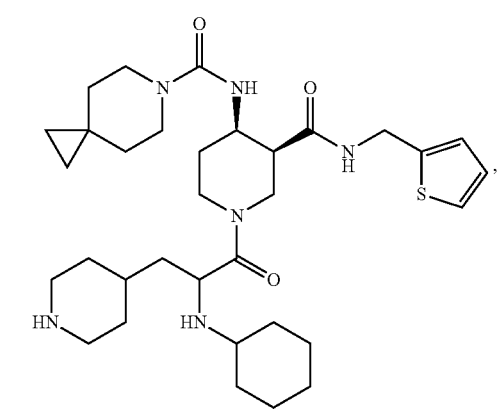
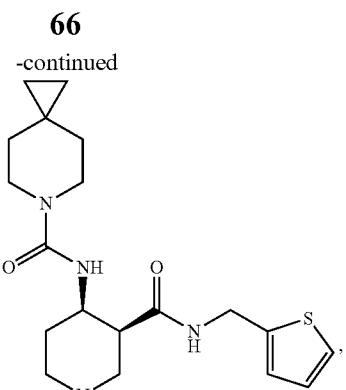
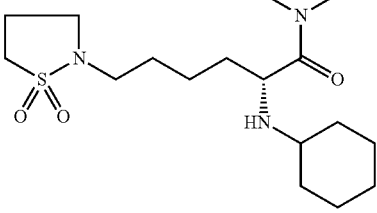
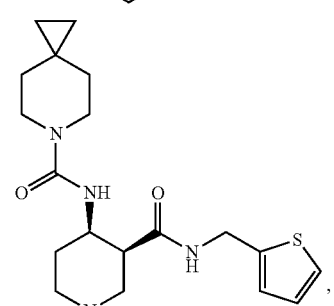
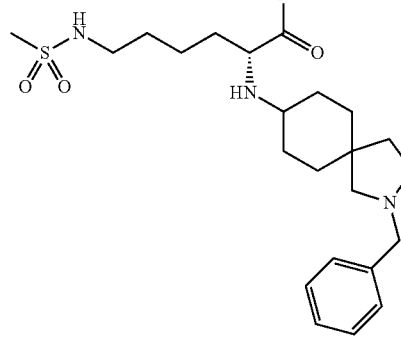
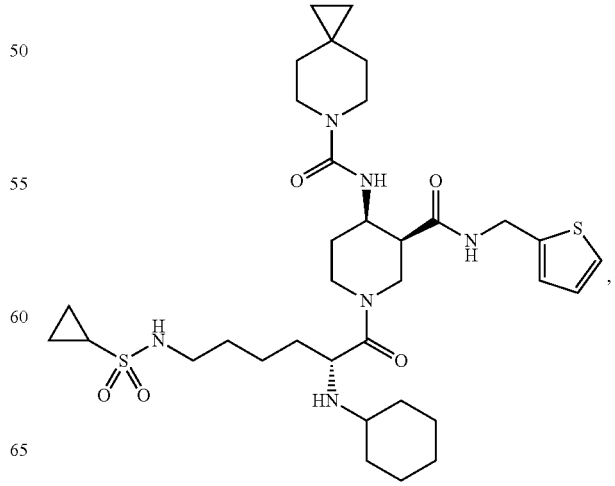
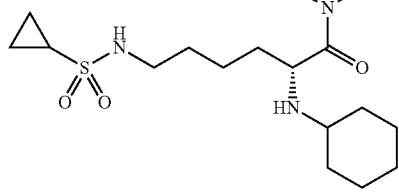

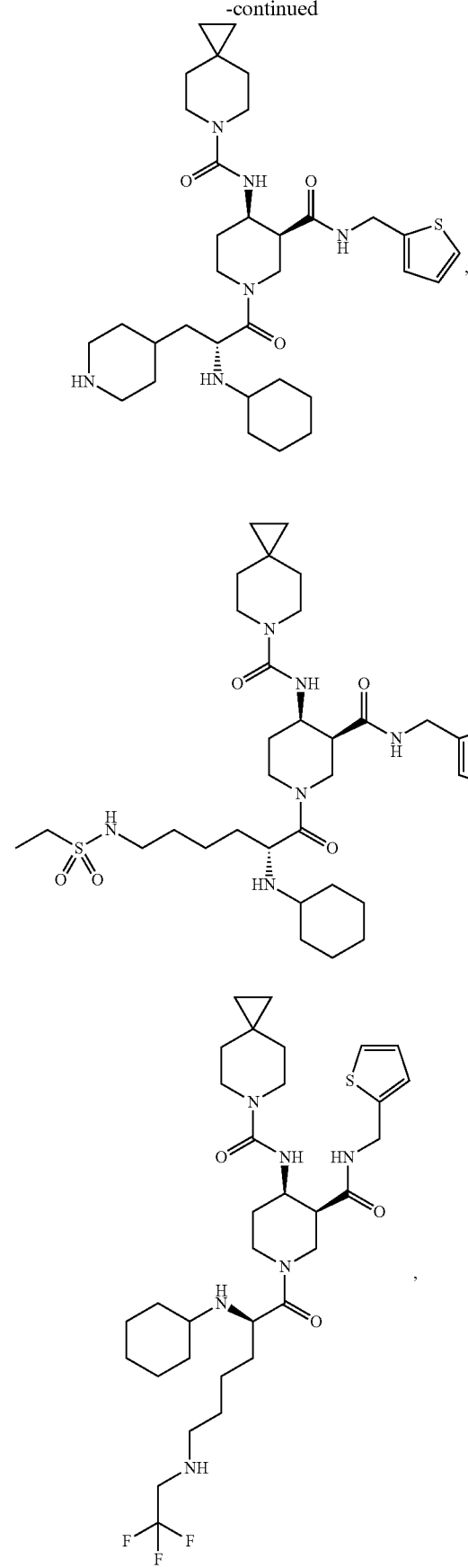
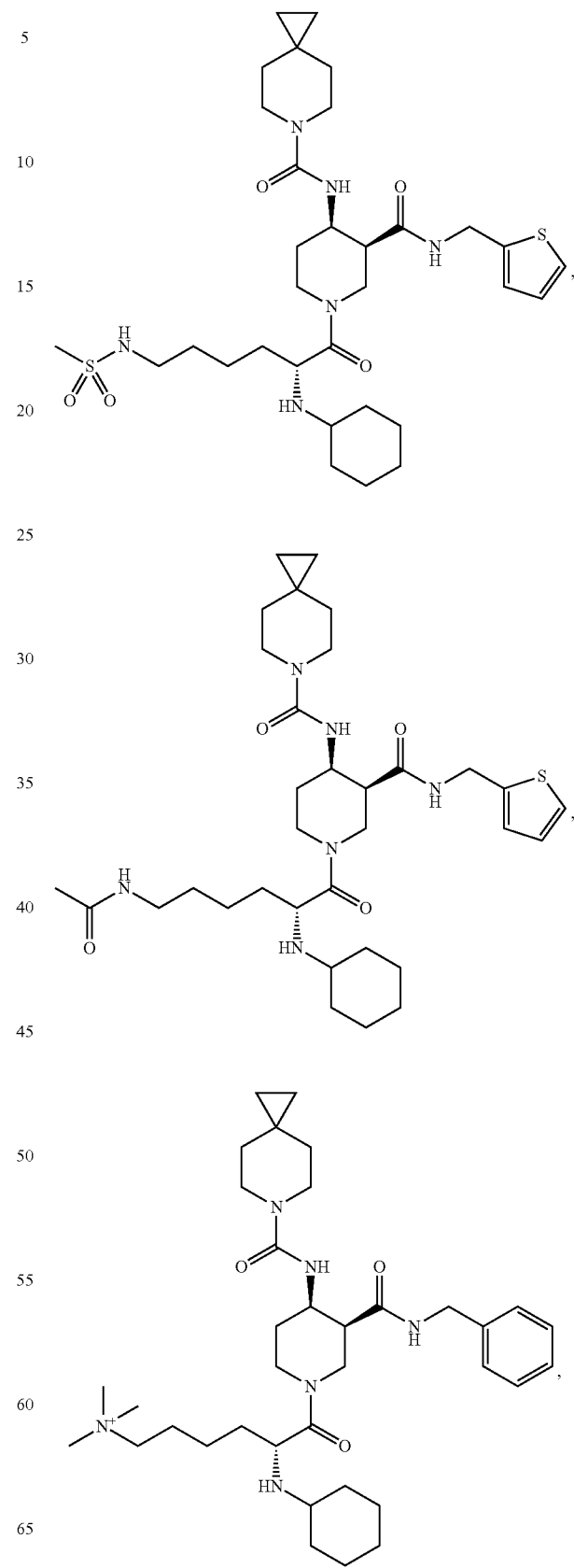

69
-continued
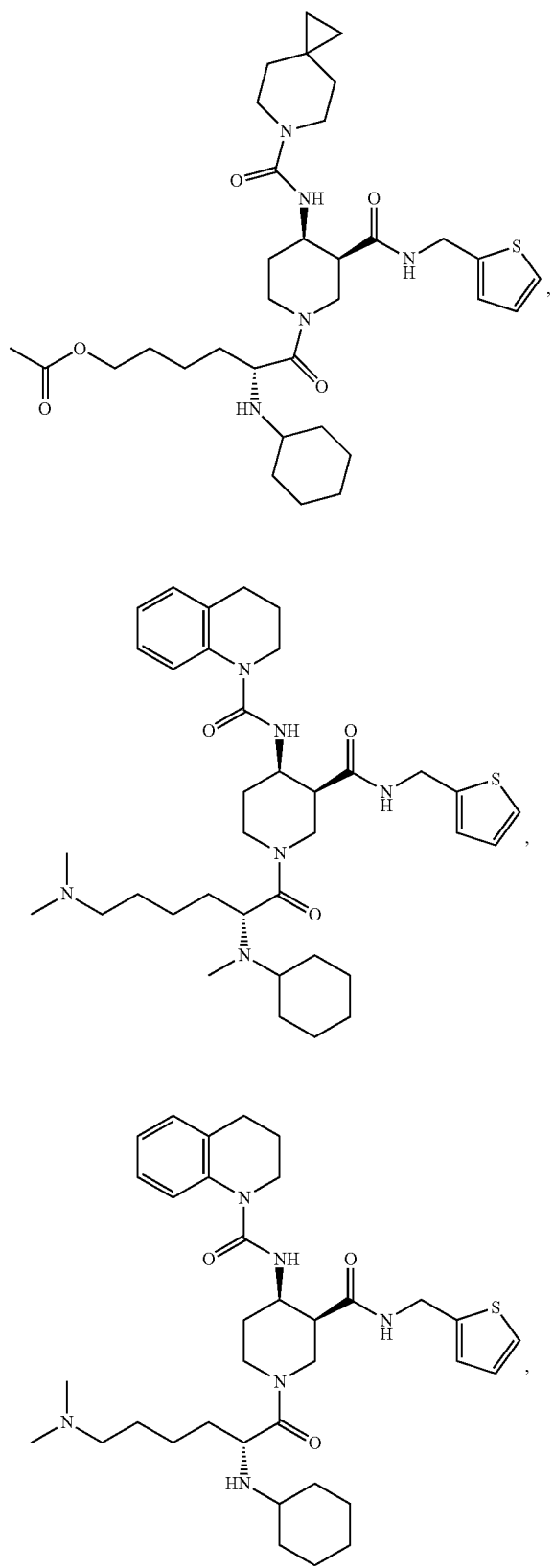
70
-continued
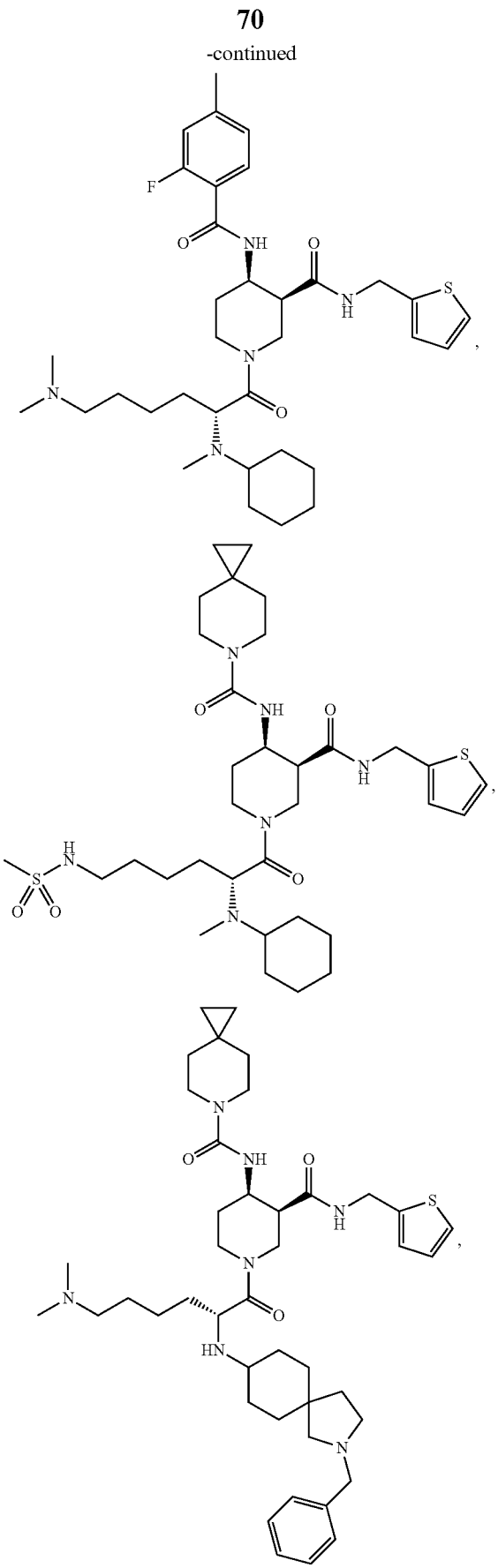

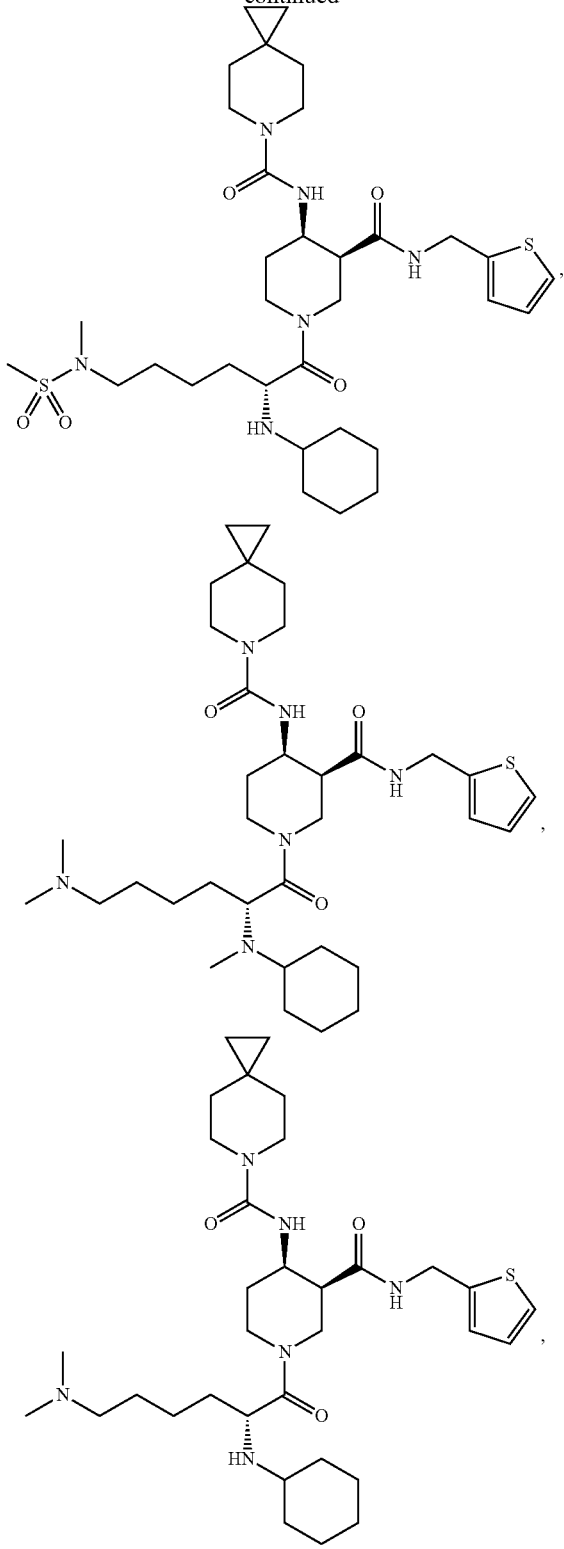

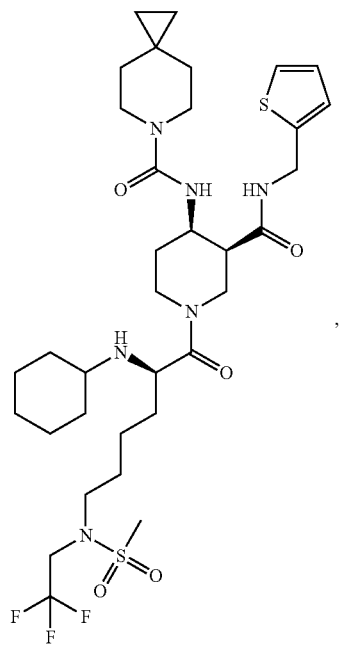

or a pharmaceutically acceptable salt thereof.

9. A pharmaceutical composition comprising a compound of claim 1 or a pharmaceutically acceptable salt thereof and a pharmaceutically acceptable carrier.

10. A method for inhibiting thrombus formation in blood or treating thrombus formation in blood comprising administering a composition of claim 9 to a mammal in need of thereof.

11. A method for preventing thrombus formation in blood comprising administering a composition of claim 9 to a mammal in need thereof.

12. A method of treating venous thromboembolism and pulmonary embolism in a mammal comprising administering a composition of claim 9 to a mammal in need thereof.

13. A method of treating deep vein thrombosis in a mammal comprising administering a composition of claim 9 to a mammal in need thereof.

14. A method of treating thromboembolic stroke in a human comprising administering a composition of claim 9 to a mammal in need thereof.

* * * * *